(12) United States Patent
Matsuyama et al.

(10) Patent No.: US 9,181,217 B2
(45) Date of Patent: Nov. 10, 2015

(54) METHOD FOR PRODUCING OPTICALLY ACTIVE NAPHTHALENE COMPOUND

(75) Inventors: Koji Matsuyama, Osaka (JP); Masanori Hatsuda, Osaka (JP); Masahiko Yoshinaga, Osaka (JP); Mitsuhiro Yada, SanyoOnoda (JP); Koichi Tanimoto, Osaka (JP)

(73) Assignee: MITSUBISHI TANABE PHARMA CORPORATION, Osaka-Shi (JP)

( * ) Notice: Subject to any disclaimer, the term of this patent is extended or adjusted under 35 U.S.C. 154(b) by 12 days.

(21) Appl. No.: 14/240,466

(22) PCT Filed: Aug. 24, 2012

(86) PCT No.: PCT/JP2012/071493
§ 371 (c)(1),
(2), (4) Date: Feb. 24, 2014

(87) PCT Pub. No.: WO2013/027835
PCT Pub. Date: Feb. 28, 2013

(65) Prior Publication Data
US 2015/0152082 A1   Jun. 4, 2015

(30) Foreign Application Priority Data

Aug. 25, 2011   (JP) ................................. 2011-183867

(51) Int. Cl.
C07B 53/00    (2006.01)
C07C 25/06    (2006.01)
C07C 255/03   (2006.01)
C07D 401/04   (2006.01)

(52) U.S. Cl.
CPC .............. *C07D 401/04* (2013.01); *C07B 53/00* (2013.01); *C07C 25/06* (2013.01); *C07C 255/03* (2013.01)

(58) Field of Classification Search
None
See application file for complete search history.

(56) References Cited

U.S. PATENT DOCUMENTS

| 5,969,140 | A  | 10/1999 | Ukita et al. |
| 7,989,627 | B2 | 8/2011  | Okamoto et al. |
| 2009/0269821 | A1 | 10/2009 | Okamoto et al. |
| 2010/0130494 | A1 | 5/2010  | Naotsuka et al. |

FOREIGN PATENT DOCUMENTS

| JP | 9-059255 A | 3/1997 |
| JP | 10-226647 A | 8/1998 |
| WO | WO 2006/046774 A1 | 5/2006 |
| WO | WO 2007/040238 A1 | 4/2007 |
| WO | WO 2007/040240 A1 | 4/2007 |
| WO | WO 2007/043426 A1 | 4/2007 |

OTHER PUBLICATIONS

Translations of the International Preliminary Report on Patentability and Written Opinion of the International Searching Authority (Forms PCT/IB/338, PCT/IB/373 and PCT/ISA/237), dated Mar. 6, 2014, for International Application No. PCT/JP2012/071493.

International Search Report issued in PCT/JP2012/071493, mailed on Sep. 18, 2012.
Extended European Search Report for Appl. No. 14198529.1 dated Apr. 2, 2015.
Extended European Search Report for Appl. No. 12826351.4 dated Oct. 21, 2014.
Hashiguchi, S. et al., "Asymmetric Transfer Hydrogenation of Aromatic Ketones Catalyzed by Chiral Ruthenium(II) Complexes," J. Am. Chem. Soc., 1995, vol. 117, pp. 7562-7563.
Quallich, G. J. et al, "Enantioselective Oxazaborolidine Reduction of Ketones Containing Heteroatoms," Tetrahedron Letters, 1993, vol. 34, No. 5, pp. 785-788.

*Primary Examiner* — Timothy R Rozof
(74) *Attorney, Agent, or Firm* — Birch, Stewart, Kolasch & Birch, LLP

(57) ABSTRACT

The present invention provides an industrially advantageous method for producing an optically active naphthalene compound useful as a therapeutic agent for dermatitis or the like. Specifically, the present invention provides a method for producing an optically active naphthalene compound [I], which comprises: a step of reacting a compound [a-1] and a compound [b-1] with each other in the presence of a base and a catalyst that is composed of a Pd compound and a tertiary phosphine ligand (step a); a step of asymmetrically hydrogenating a compound [c-1] in the presence of a hydrogen donor and a complex that is prepared from a ruthenium compound and a chiral ligand, or alternatively in the presence of an optically active oxazaborolidine compound (a CBS catalyst) and a boron hydride compound (step b); and a step of treating a compound [d-1] with a reducing agent (step c). (In the above formulae, $R^a$ and $R^b$ represent the same or different lower alkyl groups; and $X^1$ represents a halogen atom.).

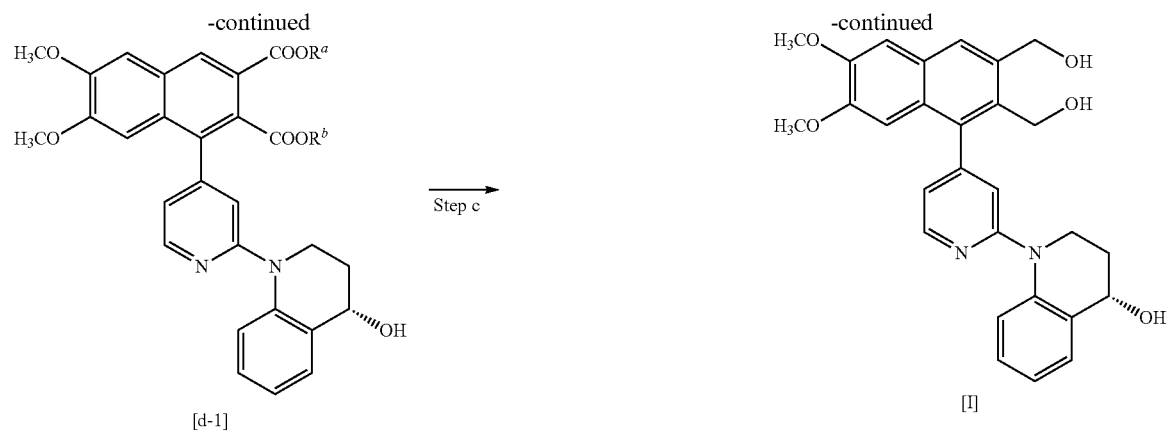
36 Claims, No Drawings

METHOD FOR PRODUCING OPTICALLY ACTIVE NAPHTHALENE COMPOUND

TECHNICAL FIELD

The present invention relates to an industrially advantageous method for producing an optically active naphthalene compound which is useful as an agent for treatment of dermatitis and the like.

BACKGROUND ART

An optically active naphthalene compound of the following formula [I]:

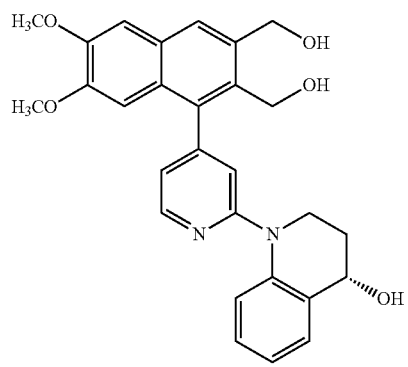

[I]

or a pharmaceutically acceptable salt thereof or a hydrate thereof shows an excellent selective phosphodiesterase 4 (PDE4) inhibitory activity, thereby is useful as an agent for treatment of an inflammatory skin disease such as atopic dermatitis and the like (Patent Literature 1). A below-mentioned method for preparing said compound in an industrial scale is proposed in Patent Literature 2.

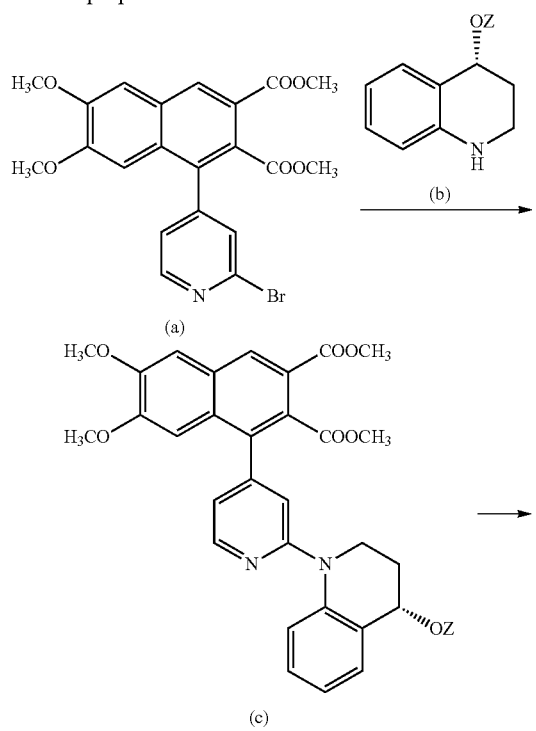

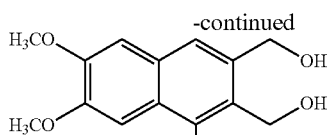

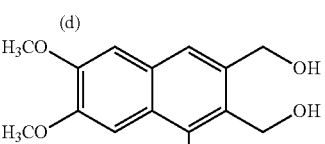

In the above scheme, Z represents a hydroxy-protecting group such as tert-butyldimethylsilyl group.

While the optically active tetrahydroquinoline compound (b) is an essential substrate compound in the above-mentioned method, the Patent Literature 2 discloses a synthetic process for producing said compound comprising the below-mentioned four steps.

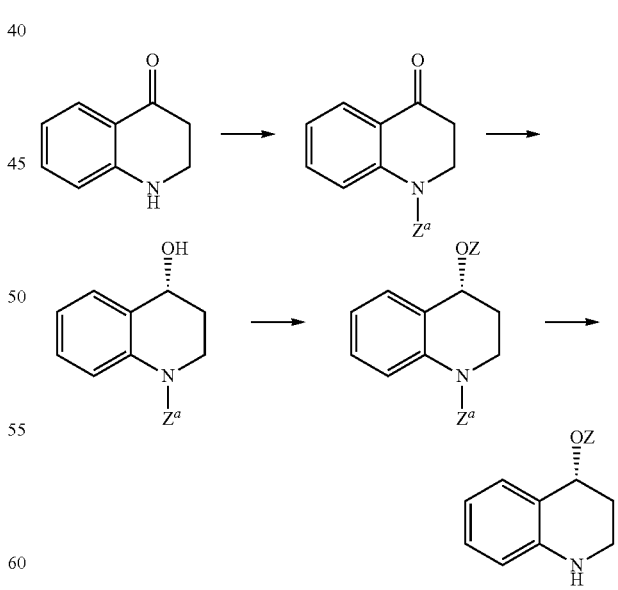

In the above scheme, $Z^a$ represents benzyloxycarbonyl group and Z represents a hydroxy-protecting group such as tert-butyldimethylsilyl group.

The method disclosed in Patent Literature 2 is therefore that for producing the optically active naphthalene compound

[I] which consists of seven steps including four steps necessary for producing the optically active tetrahydroquinoline compound (b).

BACKGROUND ART DOCUMENTS

Patent Literatures

Patent Literature 1: WO2007/043426
Patent Literature 2: European Patent Publication No. 748805A

SUMMARY OF THE INVENTION

Problems to be Solved by the Invention

The present invention provides a novel synthetic process which is industrially advantageous for producing the optically active naphthalene compound [I].

Means for Solving the Problems

As a result of intensive studies, the present inventors have accomplished the present invention by discovering an industrially advantageous method of producing the optically active naphthalene compound [I] without using the above-mentioned optically active tetrahydroquinoline compound (b).

Namely, the present invention relates to:
(1) a method of producing an optically active naphthalene compound of the following formula [I]:

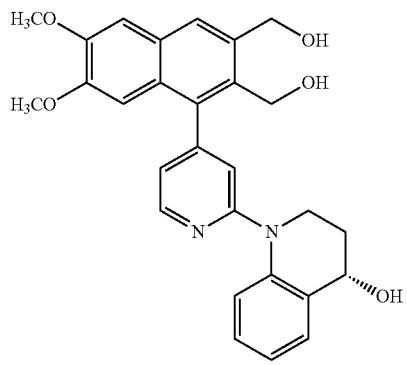

which comprises the following steps of:
(step a) reacting a compound of the following formula [a-1]:

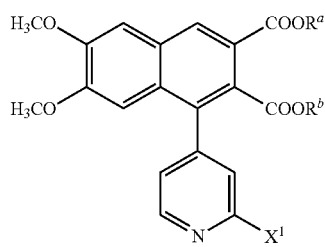

wherein $R^a$ and $R^b$ are the same or different and each of them is a lower alkyl group and $X^1$ is a halogen atom with a compound of the following formula [b-1]:

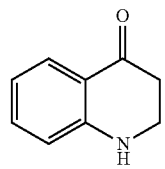

in the presence of a catalyst comprising a palladium compound and a tertiary phosphine ligand and a base and in the presence or absence of water or a water-donating substance to produce a compound of the following formula [c-1]:

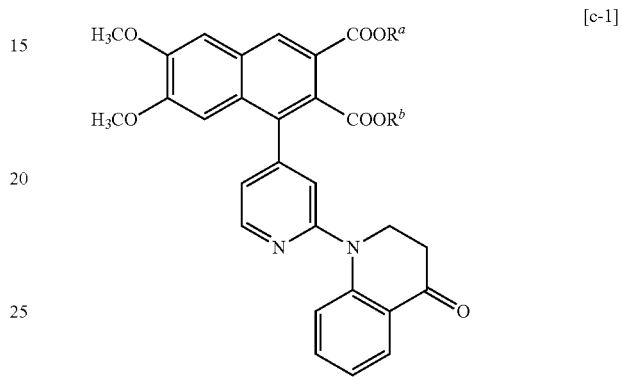

wherein the symbols are the same as defined above
or a solvate thereof,
(step b) subjecting the above compound [c-1] or a solvate thereof to
(A) an asymmetric hydrogenation in the presence of a ruthenium complex (a chiral ruthenium catalyst) prepared from a ruthenium compound and a chiral ligand and a hydrogen donor and in the presence or absence of a base; or
(B) an asymmetric hydrogenation in the presence of an optically active oxazaborolidine compound (a CBS catalyst) of the following formula [R—CBS]:

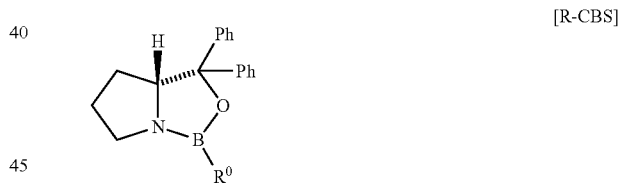

wherein Ph represents a phenyl group and $R^0$ is a lower alkyl group or a phenyl group and a boron hydride compound to produce a compound of the following formula [d-1]:

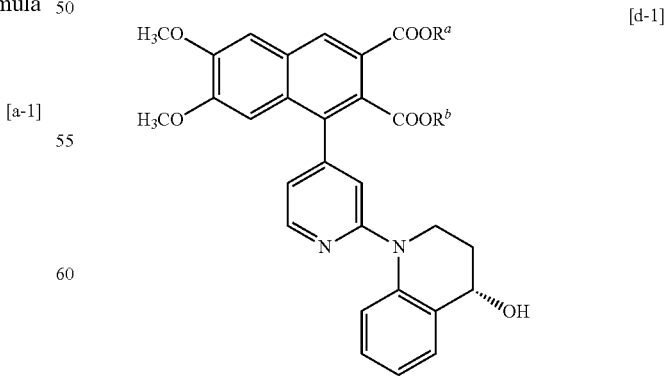

wherein the symbols are the same as defined above, or a solvate thereof, and (step c) treating the above compound [d-1] or a solvate thereof with a reducing agent;

(2) the method according to the above item (1) in which the water-donating substance in the step a is sodium sulfate decahydrate or a hydrated zeolite;

(3) the method according to the above item (1) or (2) in which the asymmetric hydrogenation in the step b is carried out in the presence of a ruthenium complex (a chiral ruthenium catalyst) prepared from a ruthenium compound and a chiral ligand and a hydrogen donor and in the presence or absence of a base;

(4) the method according to the above item (1) or (2) in which the asymmetric hydrogenation in the step b is carried out in the presence of an optically active oxazaborolidine compound [R—CBS] and a boron hydride compound;

(5) the method according to the above item (3) in which, in the step a, the palladium compound is palladium acetate, the tertiary phosphine ligand is a monodentate or bidentate phosphine ligand of the following formula [L-1]:

[L-1]

wherein $R^{O1}$ represents a phenyl group, a tert-butyl group or a cyclohexyl group, Q represents (a) a phenylene group, (b) a biphenylene group optionally substituted by a group selected from the group consisting of a halogen atom and a methoxy group, (c) a ferrocenyl group or (d) a 9,9-dimethylxanthenyl group and $R^{O2}$ represents a diphenylphosphino group, a di-tert-butyl-phosphino group or a dimethylamino group and the base is potassium carbonate, cesium carbonate or potassium phosphate, in the step b, the ruthenium complex prepared from a ruthenium compound and a chiral ligand is a ruthenium-arene complex prepared from a ruthenium compound selected from the group consisting of tetrachlorobis(benzene)diruthenium ([RuCl$_2$(C$_6$H$_6$)]$_2$), tetrachlorobis(p-cymene)diruthenium ([RuCl$_2$(C$_{10}$H$_{14}$)]$_2$), tetrachlorobis(hexamethyl benzene) diruthenium ([RuCl$_2$(C$_{12}$H$_{18}$)]$_2$), tetrachlorobis(mesitylene) diruthenium ([RuCl$_2$(C$_9$H$_{12}$)]$_2$), tetrachlorobis(ethylbenzoate)diruthenium ([RuCl$_2$(C$_9$H$_{10}$O$_2$)]$_2$), tetrabromobis (benzene)diruthenium ([RuBr$_2$(C$_6$H$_6$)]$_2$), tetrabromobis(p-cymene)diruthenium ([RuBr$_2$(C$_{10}$H$_{14}$)]$_2$), tetrabromobis (mesitylene)diruthenium ([RuBr$_2$(C$_9$H$_{12}$)]$_2$), tetraiodobis (benzene)diruthenium ([RuI$_2$(C$_6$H$_6$)]$_2$), tetraiodobis(p-cymene)diruthenium ([RuI$_2$(C$_{10}$H$_{14}$)]$_2$) and tetraiodobis (mesitylene)diruthenium ([RuI$_2$(C$_9$H$_{12}$)]$_2$), and an optically active ethylenediamine compound of the following formula [A]:

[A]

wherein $R^A$ and $R^B$ are each independently a lower alkyl group optionally having a substituent(s), an aryl group optionally having a substituent(s) or an aromatic heterocyclic group optionally having a substituent(s), or both of them combine together to form a cyclic group, $R^C$ and $R^D$ are each independently a hydrogen atom, a lower alkyl group optionally having a substituent(s), an acyl group, a carbamoyl group optionally having a substituent(s), a thioacyl group, a thiocarbamoyl group optionally having a substituent(s), a lower alkylsulfonyl group optionally having a substituent(s), an aryl-lower alkylsulfonyl group optionally having a substituent(s) or an arylsulfonyl group optionally having a substituent(s), and asterisk (*) represents an asymmetric carbon atom, the hydrogen donor is one or more compounds selected from the group consisting of an alcohol and a formic acid compound and the base is a tertiary amine, and in the step c, the reducing agent is a boron hydride compound;

(6) the method according to the above item (5) in which the tertiary phosphine ligand is 1,2-bis(diphenylphosphino)benzene, 2,2'-bis(diphenylphosphino)biphenyl, 2,2'-bis(diphenylphosiphino)-5,5'-dichloro-6,6'-dimethoxy-1,1'-biphenyl (Cl-MeO-BIPHEP), 1,1'-bis(di-tert-butyl-phosphino)ferrocene, 4,5-bis(diphenylphosphino)-9,9-dimethyl xanthene or 2-(dicyclohexylphosphino)-2'-(dimethylamino)biphenyl;

(7) the method according to the above item (5) in which the optically active ethylenediamine compound is a compound of the following formula [A-1]:

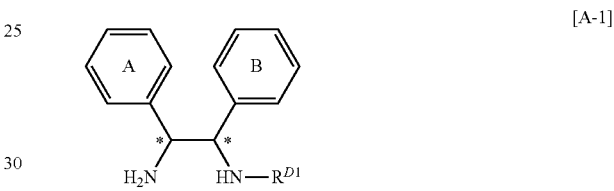

[A-1]

wherein ring A and ring B represent each independently a benzene ring optionally substituted by one to five groups selected from the group consisting of a lower alkyl group, a halogen atom and a lower alkoxy group and $R^{D1}$ represents a lower alkylsulfonyl group, a phenyl-lower alkylsulfonyl group or a lower alkylphenylsulfonyl group and the other symbols are the same as defined above;

(8) the method according to the above item (7) in which the optically active ethylenediamine compound is (S,S)—N-tosyl-1,2-diphenylethylenediamine, (S,S)—N-mesyl-1,2-diphenylethylenediamine, (S,S)—N-methyl-N'-tosyl-1,2-diphenylethylene diamine, (S,S)—N-p-methoxyphenylsulfonyl-1,2-diphenyl ethylenediamine, (S,S)—N-p-chlorophenylsulfonyl-1,2-diphenylethylenediamine, (S,S)—N-p-mesitylsulfonyl-1,2-diphenylethylenediamine, (S,S)—N-benzylsulfonyl-1,2-diphenylethylenediamine or (S,S)—N-(2,4,6-triisopropylphenyl)sulfonyl-1,2-diphenylethylenediamine;

(9) the method according to the above item (3) in which the ruthenium complex prepared from a ruthenium compound and a chiral ligand is a ruthenium-arene complex of the following formula:

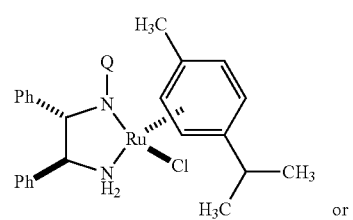

or

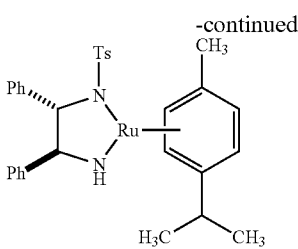

wherein Ph represents a phenyl group, Q represents a methanesulfonyl group, a p-toluenesulfonyl group or a benzylsulfonyl group and Ts represents a p-toluenesulfonyl group;

(10) the method according to the above item (3) in which the ruthenium complex prepared from a ruthenium compound and a chiral ligand is a ruthenium-arene complex of the following formula:

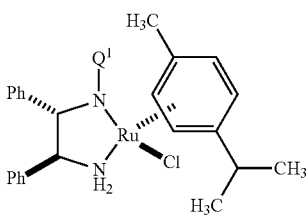

wherein Ph represents a phenyl group and $Q^1$ represents a p-toluenesulfonyl group or a benzylsulfonyl group;

(11) the method according to the above item (3) in which the palladium compound, the tertiary phosphine ligand and the base in the step a are respectively palladium acetate, 4,5-bis(diphenylphosphino)-9,9-dimethylxanthene and cesium carbonate or potassium phosphate, (i) the ruthenium complex prepared from a ruthenium compound and a chiral ligand, (ii) the hydrogen donor and (iii) the base in the step b are respectively (i) a ruthenium-arene complex of the following formula:

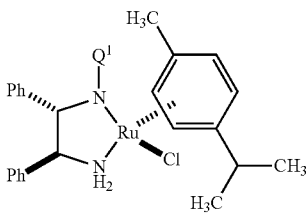

wherein Ph represents a phenyl group, $Q^1$ is a p-toluenesulfonyl group or a benzylsulfonyl group,
(ii) formic acid, potassium formate, methanol, or a mixture thereof, and (iii) triethylamine, and the reducing agent in the step c is sodium borohydride or lithium borohydride;

(12) the method according to the above item (11) in which the reaction in step a is carried out in a mixed solvent of water and an organic solvent;

(13) the method according to the above item (12) in which the mixed solvent is a mixture of water and toluene;

(14) the method according to the above item (11) in which the reaction in step a is carried out in the presence of water or a water-donating substance;

(15) the method according to the above item (14) in which the water-donating substance is sodium sulfate decahydrate or a hydrated zeolite;

(16) the method according to either one of the above items (1) to (15) in which, in the formula [a-1], $X^1$ is a bromine atom and $R^a$ and $R^b$ are each a methyl group;

(17) the method according to the above item (4) in which the optically active oxazaborolidine compound [R—CBS] is a compound of the following formula [R—CBS1]:

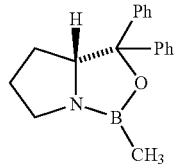

[R-CBS1]

wherein Ph represents a phenyl group,
and the boron hydride compound is a borane complex selected from the group consisting of a borane-tetrahydrofuran complex, a borane-dimethylsulfide complex, a borane-dimethylaniline complex, a borane-diethylaniline complex, a borane-tert-butylamine complex, a borane-triethylamine complex, a borane-pyridine complex and a borane-4-phenylmorpholine complex;

(18) the method according to the above item (17) in which the boron hydride compound is a borane complex selected from the group consisting of a borane-tetrahydrofuran complex, a borane-dimethylsulfide complex, a borane-diethylaniline complex and a borane-tert-butylamine complex;

(19) the method according to the above item (16) or (17) in which the reaction in the step b is carried out in a solvent selected from the group consisting of dichloromethane and tetrahydrofuran;

(20) the method according to the above item (1) in which
the reaction of the compound [a-1] with the compound [b-1] is carried out in the presence of a catalyst comprising palladium acetate and 4,5-bis(diphenylphosphino)-9,9-dimethyxanthene, and cesium carbonate or tripotassium phosphate as the base and in the presence of water or sodium sulfate decahydrate as the water-donating substance in a solvent selected from the group consisting of toluene and dimethoxyethane,
the asymmetric hydrogenation of the compound [c-1] or a solvate thereof is carried out in the presence of a ruthenium-arene complex of the following formula:

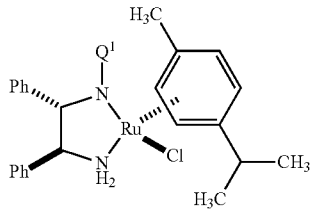

wherein Ph represents a phenyl group and $Q^1$ represents a p-toluenesulfonyl group or a benzylsulfonyl group
and one or more compounds as the hydrogen donor selected from the group consisting of formic acid, potassium formate and methanol, and in the presence or absence of triethylamine as the base in a solvent selected from the group consisting of tetrahydrofuran, dimethylacetamide, dimethoxyethane, 2-methyltetrahydrofuran, chlorobenzene, methanol and ethyl acetate, and the reducing reaction of the compound [d-1] or a solvate thereof is carried out in the presence of sodium borohydride as the reducing agent in tetrahydrofuran containing methanol as an additive;

(21) the method according to either one of the above items (1) to (20) in which, in the general formula [a-1], $R^a$ and $R^b$ are each a methyl group and $X^1$ is a bromine atom;

(22) the method according to the above item (21) in which the solvate of the compound [c-1] is a chlorobenzene monosolvate, a toluene monosolvate or a chloroform monosolvate, and the solvate of the compound [d-1] is an acetonitrile monosolvate;

(23) the method according to the above item (21) in which a further step of adding water to an ethanol solution of the compound [I] as a reaction product of the step c, followed by collecting the precipitated crystals of compound [I] in a form of 3/2 hydrate is included therein;

(24) a method of producing a 3/2 hydrate of a compound of the following formula [I-b]:

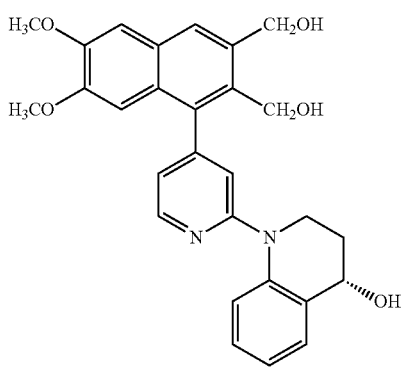
[I-b]

which comprises the following steps of:
(i) reacting a compound of the following formula [a-11]:

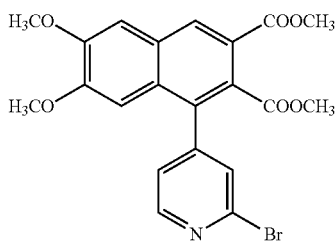
[a-11]

with a compound of the following formula [b-1]:

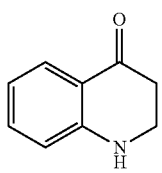
[b-1]

in a solvent in the presence of a catalyst comprising a palladium compound and a tertiary phosphine ligand and a base to produce a compound of the following formula [c-11]:

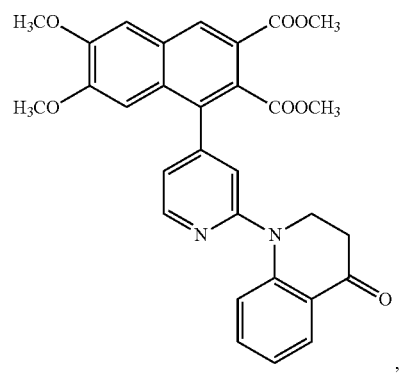
[c-11]

followed by separating and collecting crystals of said compound or a solvate thereof, (ii) subjecting the compound [c-11] or a solvate thereof obtained in the above step (i) to an asymmetric hydrogenation in the presence of a ruthenium complex prepared from a ruthenium compound and a chiral ligand and a hydrogen donor and in the presence or absence of a base to produce a compound of the following formula [d-11]:

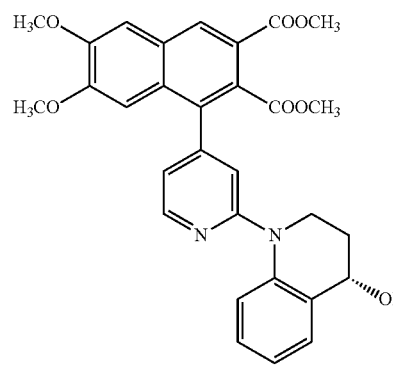
[d-11]

followed by separating and collecting crystals of said compound or a solvate thereof, (iii) treating the compound [d-11] or a solvate thereof obtained in the above step (ii) with a reducing agent in a solvent to produce the compound of the above formula [1-b]; and (iv) crystallizing said reaction product, followed by separating and collecting the obtained crystals;

(25) the method according to the above item (24) in which the solvate of the compound [c-11] is a chlorobenzene monosolvate, a toluene monosolvate or a chloroform monosolvate, and the solvate of the compound [d-11] is an acetonitrile monosolvate;

(26) the method according to the above item (24) in which the catalyst comprising a palladium compound and a tertiary phosphine ligand is a catalyst prepared from palladium acetate and a monodentate or bidentate phosphine ligand of the following formula [L-1]:

$(R^{O1})_2P\text{-}Q\text{-}R^{O2}$ [L-1]

wherein $R^{O1}$ represents a phenyl group, a tert-butyl group or a cyclohexyl group, Q represents (a) a phenylene group, (b) a biphenylene group optionally substituted by a group selected from the group consisting of a halogen atom and a methoxy group, (c) a ferrocenyl group or (d) a 9,9-dimethylxanthenyl group and $R^{02}$ represents a diphenylphosphino group, a di-tert-butyl-phosphino group or a dimethylamino group, the ruthenium complex prepared from a ruthenium compound and a chiral ligand is a ruthenium-arene complex of the following formula:

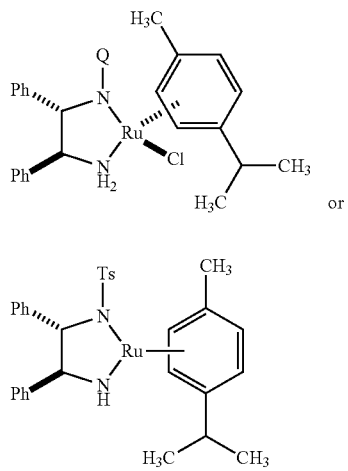

or wherein Ph represents a phenyl group, Q represents a methanesulfonyl group, a p-toluenesulfonyl group or a benzylsulfonyl group and Ts represents a p-toluenesulfonyl group, and the reducing agent is sodium borohydride or lithium borohydride;

(27) the method according to the above item (26) in which the reaction of the compound [a-11] with the compound [b-1] is carried out in a solvent selected from the group consisting of toluene, tetrahydrofuran, dimethylformamide, cyclopentyl methyl ether, chlorobenzene, tert-butanol, N-methylpyrrolidinone, dimethoxyethane and a mixture thereof, the asymmetric hydrogenation of the compound [c-11] or a solvate thereof is carried out in a solvent selected from the group consisting of tetrahydrofuran, 2-methyltetrahydrofuran, 1,2-dimethoxyethane, acetonitrile, chlorobenzene, dimethyl formamide, dimethylacetamide, ethyl acetate, isopropyl acetate, methanol and pyridine, and the reducing reaction of the compound [d-11] or a solvate thereof is carried out in a solvent selected from the group consisting of tetrahydrofuran, toluene and a mixture thereof;

(28) the method according to the above item (24) in which the reaction of the compound [a-11] with the compound [b-1] is carried out in the presence of a catalyst comprising palladium acetate and 4,5-bis(diphenylphosphino)-9,9-dimethylxanthene and cesium carbonate or tripotassium phosphate as the base in a solvent selected from the group consisting of toluene and dimethoxyethane, the asymmetric hydrogenation of the compound [c-11] or a solvate thereof is carried out in the presence of a ruthenium-arene complex of the following formula:

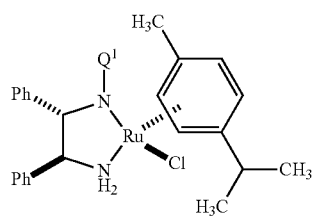

wherein Ph represents a phenyl group and $Q^1$ is a p-toluenesulfonyl group or a benzylsulfonyl group and one or more compound(s), as the hydrogen donor, selected from the group consisting of formic acid, potassium formate and methanol and in the presence or absence of triethylamine as the base in a solvent selected from the group consisting of tetrahydrofuran, dimethylacetamide, dimethoxyethane, 2-methyltetrahydrofuran, chlorobenzene, methanol and ethyl acetate, and the reducing reaction of the compound [d-11] or a solvate thereof is carried out in the presence of sodium borohydride as the reducing agent in tetrahydrofuran containing methanol as an additive;

(29) the method according to the above item (24) in which the asymmetric hydrogenation of the compound [c-11] or a solvate thereof is carried out in methanol, N-methylpyrrolidone, water or a mixture thereof as the solvent;

(30) the method according to the above item (24) in which the asymmetric hydrogenation of the compound [c-11] or a solvate thereof is carried out in the presence of methanol as the hydrogen donor and in dichloromethane, N-methylpyrrolidinone or 1,3-dimethylimidazolidinone as the solvent;

(31) the method according to the above item (28) in which the asymmetric hydrogenation of the compound [c-11] or a solvate thereof is carried out in the presence of potassium formate and methanol as the hydrogen donor and in chlorobenzene as the solvent;

(32) the method according to the above item (28) in which the asymmetric hydrogenation of the compound [c-11] or a solvate thereof is carried out in the presence of formic acid as the hydrogen donor and in tetrahydrofuran as the solvent;

(33) a compound of the following formula [c-11]:

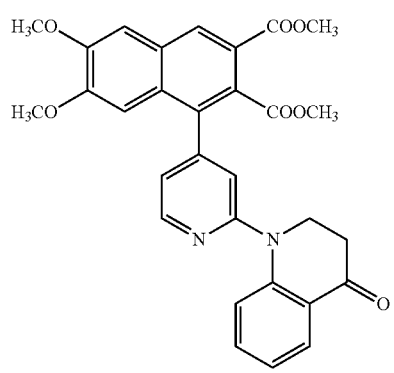

[c-11]

or a solvate thereof.

(34) a chlorobenzene monosolvate, a toluene monosolvate or a chloroform monosolvate of the compound [c-11] according to the above item (33);

(35) a compound of the following formula [d-11]:

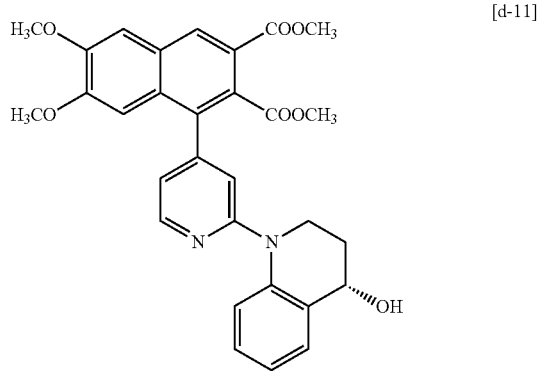 [SMILES: COC(=O)c1cc2cc(OC)c(OC)cc2c(-c2ccnc(N3CC[C@H](O)c4ccccc43)c2)c1C(=O)OC]

or a solvate thereof; and

(36) an acetonitrile monosolvate of the compound [d-11] according to the above item (35).

Embodiments to Carry Out the Invention

Step a

The present step can be carried out in a solvent which does not disturb the reaction and examples of the solvent include an aromatic hydrocarbon such as toluene or chlorobenzene, an ether such as tetrahydrofuran, dimethoxyethane or cyclopentyl methyl ether, an amide such as dimethylformamide, an alcohol such as tert-butanol, N-methylpyrrolidinone and a mixture thereof. Among them, toluene or a mixture of toluene and tert-butanol is preferable. Water or a water-donating substance can be optionally added to the above solvent. In case of using a mixture of the above solvent and water, amount of water to an organic solvent can be in the range of 0.6 v/w % to 2.2 v/w %, preferably 1.1 v/w % to 1.6 v/w %. Besides, any compounds which supply water to the reaction system and do not disturb said reaction can be used as the water-donating substance. Examples of said water-donating substance include a compound in a form of hydrate such as sodium sulfate decahydrate, a hydrated zeolite (trade name: Celite) and the like. Amount of the water-donating substance to be added, while dependent on its adhesive water content, for example, the amount of sodium sulfate decahydrate can be in the range of 0.26 to 0.85 molar equivalent, preferably 0.60 to 0.72 molar equivalent to the compound [a-1] or the compound [a-11]. The hydrated zeolite as a water-donating substance can be prepared by suspending dry zeolite in a reaction system followed by adding dropwise a desired amount of water thereto under stirring.

Examples of the catalyst used in the present step comprising a palladium compound and a tertiary phosphine ligand include a catalyst comprising palladium acetate and a tertiary phosphine ligand. Examples of said tertiary phosphine ligand include a monodentate or bidentate phosphine ligand of the following formula [L-1]:

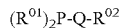    [L-1]

wherein $R^{01}$ represents a phenyl group, a tert-butyl group or a cyclohexyl group, Q represents (a) a phenylene group, (b) a biphenylene group optionally substituted by a group selected from the group consisting of a halogen atom and a methoxy group, (c) a ferrocenyl group or (d) a 9,9-dimethylxanthenyl group and $R^{02}$ represents a diphenylphosphino group, a di-tert-butyl-phosphino group or a dimethylamino group. Concrete examples of said phosphine ligand [L-1] include a bidentate phosphine ligand such as 1,2-bis(diphenylphosphino)benzene (Ligand-1), 2,2'-bis(diphenylphosphino)biphenyl (BIPHEP), 2,2'-bis(diphenylphosphino)-5,5'-dichloro-6,6'-dimethoxy-1,1'-biphenyl (Cl-MeO-BIPHEP), 1,1'-bis(di-tert-butyl-phosphino)ferrocene (DtBPF) or 4,5-bis(diphenylphosphino)-9,9-dimethylxanthene (Xantphos) and a monodentate phosphine ligand such as 2-(dicyclohexylphosphino)-2'-(dimethylamino)biphenyl (Dave-Phos). Among these ligands, the bidentate phosphine ligand is preferable and 4,5-bis(diphenylphosphino)-9,9-dimethylxanthene is particularly preferable.

Examples of the base used in the step a include potassium carbonate, cesium carbonate and potassium phosphate (e.g., tripotassium phosphate), and among them, cesium carbonate or tripotassium phosphate is preferable.

Amount of the above catalyst (palladium basis) can be in the range of 0.005 molar equivalent to 0.200 molar equivalent, preferably 0.01 molar equivalent to 0.05 molar equivalent to the compound [a-1] (or the compound [a-11]) or the compound [b-1]. Amount of the tertiary phosphine ligand can be in the range of 0.5 molar equivalent to 2.5 molar equivalent, preferably 1.0 molar equivalent to 1.5 molar equivalent to the palladium compound. Amount of the above base can be in the range of 1.5 molar equivalent to 5.0 molar equivalent, preferably 2.5 molar equivalent to 3.5 molar equivalent to the compound [a-1] (or the compound [a-11]) or the compound [b-1]. The present reaction can be carried out at 40° C. to 100° C., preferably 45° C. to 65° C.

The objective compound [c-1] or the compound [c-11] in the step a can be separated and collected from the reaction mixture by using any known or conventional method. For example, the compound [c-1] can be obtained by adding a poor solvent such as n-heptane, water or a mixture thereof to the reaction mixture containing said compound, collecting the resultant precipitates, washing and drying thereof. Impurities such as by-products (e.g., analogues of the objective compound [c-1] or [c-11] and the like) can be removed by treating the obtained objective compound [c-1] or the compound [c-11] with an adsorbent such as silica gel or activated charcoal in a good solvent such as chlorobenzene or tetrahydrofuran. Besides, the compound [c-1] or the compound [c-11] can be obtained in a form of solvate such as a chlorobenzene monosolvate, a toluene monosolvate, a chloroform monosolvate or the like. It is characterized in that the compound [c-1], the compound [c-11] or a solvate thereof can be readily crystallized, thereby it is a preferable synthetic intermediate in industrial production of the naphthalene compound [I]. For example, the impurities can be effectively removed from the product by obtaining the compound [c-1] or [c-11] in a crystalline form of a specific solvate (e.g., a toluene monosolvate), converting it to the other solvate (e.g., a chloroform monosolvate) and crystallizing, and then converting said solvate to a non-solvate form and then crystallizing thereof.

Step b (A)/Reaction with Using an Asymmetric Ruthenium Catalyst

The present step can be carried out in a solvent which does not disturb the reaction and examples of the solvent include an ether such as tetrahydrofuran, 2-methyltetrahydrofuran or 1,2-dimethoxyethane, a nitrile such as acetonitrile, an aromatic hydrocarbon such as chlorobenzene, a halogenated aliphatic hydrocarbon such as dichloromethane, an amide such as dimethylformamide, 1,3-dimethylimidazolidinone, N-methylpyrrolidone or dimethylacetamide, an ester such as ethyl acetate or isopropyl acetate, an alcohol such as methanol, pyridine, water and a mixture thereof. Among them, dichloromethane or tetrahydrofuran is preferable.

Examples of the hydrogen donor include an alcohol such as methanol or 2-propanol and a formic acid compound such as formic acid or an alkali metal formate (e.g., potassium formate). Among them, one or more compound(s) selected from the group consisting of formic acid, potassium formate and methanol are preferable. Meanwhile, in case that a formic acid compound is used as a hydrogen donor, the reaction is irreversible and such reaction can be carried out under a condition of a higher substrate concentration or a higher substrate/catalyst ratio.

Examples of the base include a tertiary amine such as a tri-lower alkyl amine (e.g., triethylamine) and triethylamine is preferable. Meanwhile, formic acid as a hydrogen donor can be used in a form of azeotropic mixture with the base (e.g., triethylamine).

Examples of the ruthenium complex used in the present step (a catalyst for asymmetric hydrogen transfer reduction) which is prepared from a ruthenium compound and a chiral ligand include a ruthenium-arene complex prepared from a ruthenium compound selected from the group consisting of tetrachlorobis(benzene)diruthenium ([RuCl$_2$(C$_6$H$_6$)]$_2$), tetrachlorobis(p-cymene)diruthenium ([RuCl$_2$(C$_{10}$H$_{14}$)]$_2$), tetrachlorobis(hexamethyl benzene)diruthenium ([RuCl$_2$(C$_{12}$H$_{18}$)]$_2$), tetrachlorobis(mesitylene)diruthenium ([RuCl$_2$(C$_9$H$_{12}$)]$_2$), tetrachlorobis(ethyl benzoate)diruthenium ([RuCl$_2$(C$_9$H$_{10}$O$_2$)]$_2$), tetrabromobis(benzene)diruthenium ([RuBr$_2$(C$_6$H$_6$)]$_2$), tetrabromobis(p-cymene)diruthenium ([RuBr$_2$(C$_{10}$H$_{14}$)]$_2$), tetrabromobis(mesitylene)diruthenium ([RuBr$_2$(C$_9$H$_{12}$)]$_2$), tetraiodobis(benzene)diruthenium ([RuI$_2$(C$_6$H$_6$)]$_2$), tetraiodobis(p-cymene)diruthenium ([RuI$_2$(C$_{10}$H$_{14}$)]$_2$) and tetraiodobis(mesitylene)diruthenium ([RuI$_2$(C$_9$H$_{12}$)]$_2$), and an optically active ethylenediamine compound of the following formula [A]:

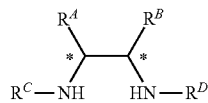

[A]

wherein the symbols are the same as defined above.

In the chiral ligand [A], examples of $R^A$ and $R^B$ include a lower alkyl group optionally having a substituent(s) such as a methyl group, a chloromethyl group, an ethyl group, a n-propyl group or an isopropyl group; an aryl group optionally having a substituent(s) such as a phenyl group, a naphthyl group, a 4-methylphenyl group, a 3,5-dimethylphenyl group or a 4-methoxyphenyl group; an aromatic heterocyclic group optionally having a substituent(s) such as a furyl group or a pyridyl group; or a cyclic group formed by combining $R^A$ and $R^B$ together such as a tetraethylene group which may be substituted by one or more group(s) selected from the group consisting of a lower alkoxy group and a halogen atom. Examples of $R^C$ and $R^D$ include a hydrogen atom; a lower alkyl group optionally having a substituent(s) such as a methyl group, a chloromethyl group, an ethyl group, a n-propyl group or an isopropyl group; an acyl group such as an acetyl group, a propionyl group or a benzoyl group; a carbamoyl group optionally having a substituent(s) such as a carbamoyl group, a methylcarbamoyl group or a phenylcarbamoyl group; a thioacyl group such as a thioacetyl group, a thiopropionyl group or a thiobenzoyl group; a thiocarbamoyl group optionally having a substituent(s) such as a thiocarbamoyl group, a methylthiocarbamoyl group or a phenylthiocarbamoyl group; an optionally substituted lower alkylsulfonyl group such as a methanesulfonyl group, a trifluoromethanesulfonyl group or an ethanesulfonyl group; an optionally substituted aryl-lower alkylsulfonyl group such as a benzylsulfonyl group or an optionally substituted arylsulfonyl group such as a benzenesulfonyl group, a toluenesulfonyl group, a 2,4,6-trimesityl sulfonyl group, a 2,4,6-triisopropylbenzenesulfonyl group, a 4-methoxybenzenesulfonyl group, a 4-chlorobenzenesulfonyl group or a 2-naphthylsulfonyl group.

Preferred examples of the above-mentioned optically active ethylenediamine compound (a chiral ligand) include an optically active alkylenediamine compound of the following formula [A-1]:

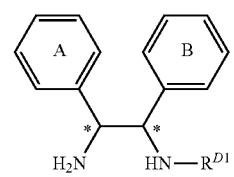

[A-1]

wherein the symbols are the same as defined above. Concrete examples of such optically active alkylenediamine compound include (S,S)—N-tosyl-1,2-diphenylethylenediamine, (S,S)—N-mesyl-1,2-diphenylethylenediamine, (S,S)—N-methyl-N'-tosyl-1,2-diphenylethylenediamine, (S,S)—N-p-methoxyphenylsulfonyl-1,2-diphenyl ethylenediamine, (S,S)—N-p-chlorophenylsulfonyl-1,2-diphenylethylenediamine, (S,S)—N-p-mesitylsulfonyl-1,2-diphenylethylenediamine, (S,S)—N-benzylsulfonyl-1,2-diphenylethylenediamine, (S,S)—N-(2,4,6-triisopropylphenyl)sulfonyl-1,2-diphenylethylenediamine and the like. Among them, (S,S)—N-tosyl-1,2-diphenylethylenediamine is preferable.

Concrete examples of the ruthenium complex prepared from a ruthenium compound and a chiral ligand include a ruthenium-arene complex such as chloro [(1S,2S)—N-(p-toluenesulfonyl)-1,2-diphenylethylenediamine](p-cymene)ruthenium(II) [RuCl[(S,S)-TsDPEN](p-cymene)]; chloro [(1S,2S)—N-(p-toluenesulfonyl)-1,2-diphenylethylenediamine](mesitylene)ruthenium(II) [RuCl[(S,S)-TsDPEN](mesitylene)]; chloro [(1S,2S)—N-(methanesulfonyl)-1,2-diphenylethylenediamine](p-cymene)ruthenium(II) [RuCl[(S,S)-MsDPEN](p-cymene)]; [(1S,2S)—N-(p-toluenesulfonyl)-1,2-diphenylethylenediamine](p-cymene)ruthenium(II) [Ru[(S,S)-TsDPEN] (p-cymene)]; [(1S,2S)—N-(p-toluenesulfonyl)-1,2-diphenylethylenediamine](mesitylene)ruthenium(II) hydride [RuH[(S,S)-TsDPEN](mesitylene)] or chloro[(1S,2S)—N-benzylsulfonyl-1,2-diphenylethylenediamine](p-cymene)ruthenium(II) [RuCl[(S,S)—BnSO$_2$DPEN](p-cymene)].

Among the above ruthenium complexes prepared from a ruthenium compound and a chiral ligand, for example, a ruthenium-arene complex of the following formula:

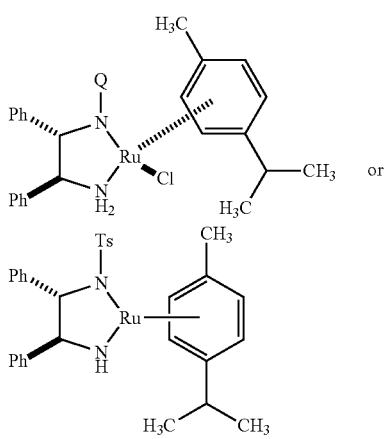

wherein the symbols are the same as defined above
is preferable, and a ruthenium-arene complex of the following formula:

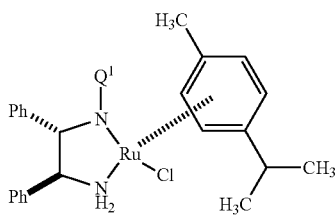

wherein the symbols are the same as defined above
is more preferable.

The above ruthenium-arene complexes are commercially available or producible by, for example, the known method disclosed in Journal of the American Chemical Society, Vol. 117, pp. 7562-7563 (1995).

Amount of the above hydrogen donor to be used can be in the range of 3 molar equivalent to 30 molar equivalent, preferably 10 molar equivalent to 20 molar equivalent to the compound [c-1] or the compound [c-11]. Amount of the above ruthenium complex prepared from a ruthenium compound and a chiral ligand to be used can be in the range of 0.005 molar equivalent to 0.200 molar equivalent, preferably 0.01 molar equivalent to 0.05 molar equivalent to the compound [c-1] or the compound [c-11].

Amount of the base to be used can be in the range of 3 molar equivalent to 20 molar equivalent, preferably 8 molar equivalent to 12 molar equivalent to the compound [c-1] or the compound [c-11]. The present reaction can be carried out at 30° C. to 70° C., preferably 45° C. to 55° C.

The objective compound [d-1] or the compound [d-11] can be separated and collected from the reaction mixture in the present step by a known or conventional method. For example, the compound [d-1] or the compound [d-11] can be obtained by treating the reaction mixture containing said compound with an appropriate quenching agent such as an acid (e.g., citric acid) if necessary, separating the organic layer and concentrating thereof, treating the resultant residue with a poor solvent such as acetonitrile and collecting the resultant precipitates.

Step b (B)/Reaction with Using a CBS Catalyst

The present step can be carried out in a solvent which does not disturb the reaction and examples of the solvent include an ether such as tetrahydrofuran and a halogenated aliphatic hydrocarbon such as dichloromethane. Among them, dichloromethane or tetrahydrofuran is preferable.

Examples of the optically active oxazaborolidine compound (a CBS catalyst) of the following formula [R—CBS]:

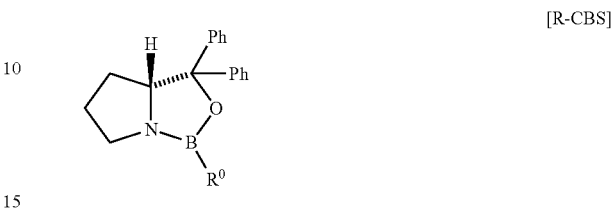

wherein the symbols are the same as defined above
include those in which $R^0$ is a lower alkyl group such as a $C_{1-4}$ alkyl group or a phenyl group. Among them, a compound in which $R^0$ is a methyl group, namely a compound of the following formula [R—CBS1]:

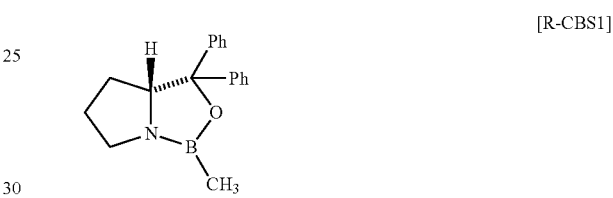

wherein Ph represents a phenyl group
is preferable.

Examples of the boron hydride compound include a borane-tetrahydrofuran complex, a borane-dimethylsulfide complex, a borane-dimethylaniline complex, a borane-diethylaniline complex, a borane-tert-butylamine complex, a borane-triethylamine complex, a borane-pyridine complex and a borane-4-phenylmorpholine complex. Among them, a borane-tetrahydrofuran complex, a borane-dimethylsulfide complex, a borane-diethylaniline complex or a borane-tert-butylamine complex is preferable, and a borane-diethylaniline complex is further preferable.

Amount of the CBS catalyst to be used in the present step can be in the range of 0.1 molar equivalent to 1.0 molar equivalent, preferably 0.3 molar equivalent to 0.6 molar equivalent to the compound [c-1] (or the compound [c-11]) or a solvate thereof. Amount of the boron hydride compound to be used can be in the range of 1.0 molar equivalent to 3.0 molar equivalent, preferably 1.5 molar equivalent to 2.0 molar equivalent to the compound [c-1] or the compound [c-11]. The present reaction can be carried out at −25° C. to 25° C., preferably −10° C. to 10° C.

Step c

The present step can be carried out in a solvent which does not disturb the reaction and examples of the solvent include an ether such as tetrahydrofuran, an aromatic hydrocarbon such as toluene and a mixture thereof. Among them, tetrahydrofuran, toluene or a mixture thereof is preferable.

The present reaction can be carried out in the presence or absence of an additive. Examples of the additive include an alcohol such as methanol, ethanol or isopropanol, and among them, methanol is preferable.

Examples of the reducing agent include metal salt of boron hydride such as sodium borohydride or lithium borohydride, and among them, sodium borohydride is preferable.

Amount of the reducing agent to be used can be in the range of 2 molar equivalent to 15 molar equivalent, preferably 4 molar equivalent to 9 molar equivalent to the compound [d-1] (or the compound [d-11]) or a solvate thereof. Amount of the additive to be used can be in the range of 6 molar equivalent to 45 molar equivalent, preferably 12 molar equivalent to 24 molar equivalent to the compound [d-1] (or the compound [d-11]) or a solvate thereof. The present reaction can be carried out at 40° C. to 60° C., preferably 45° C. to 55° C.

The objective compound [I] can be separated and collected from the reaction mixture in the present step by a known or conventional method. For example, the compound [I] can be obtained by treating the reaction mixture containing said compound with an appropriate quenching agent such as an organic solvent (e.g., acetone) or water if necessary, separating the organic layer followed by concentrating thereof, treating the resultant residue with a poor solvent such as water or ethanol, and collecting the resultant precipitates.

Meanwhile, it is characterized in that the compound [c-1] (or the compound [c-11]) or a solvate thereof such as a chlorobenzene monosolvate, a toluene monosolvate or a chloroform monosolvate and the compound [d-1] (or the compound [d-11]) or a solvate thereof such as an acetonitrile monosolvate can be readily crystallized, thereby it is a preferable synthetic intermediate in the production method of the present invention.

The starting material in a production method of the present invention, namely, the compound [a-1], can be produced, for example, by a known process disclosed in Patent Literature 2. Besides, among the compounds [a-1], a compound of the following formula [a-11]:

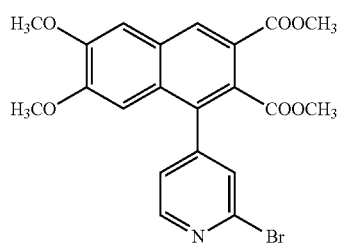

[a-11]

can be also prepared by, for example, reacting a compound of the following formula [1]:

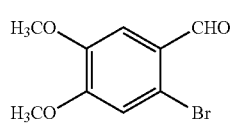

[1]

with a compound of the following formula [2]:

CH(OCH₃)₃ [2]

in the presence of p-toluenesulfonic acid monohydrate in an appropriate solvent such as an alcohol (e.g., methanol) to prepare a compound of the following formula [3]:

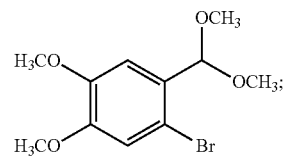

[3]

reacting the compound [3] with a compound of the following formula [4]:

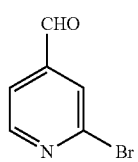

[4]

in the presence of n-butyllithium in an appropriate solvent such as an ether (e.g., tetrahydrofuran) to prepare a compound of the following formula [5]:

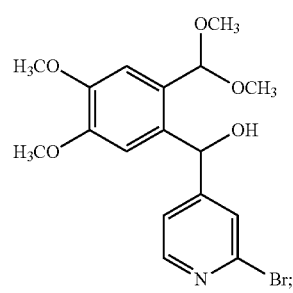

[5]

and reacting the compound [5] with a compound of the following formula [6]:

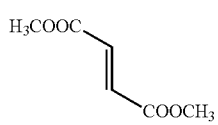

[6]

in the presence of acetic acid and boron trifluoride-diethyl ether complex in an appropriate solvent such as an aromatic hydrocarbon (e.g., xylene or toluene).

Besides, the compound [b-1] as a starting material is commercially available (CAS No.: 4295-36-7), and can be prepared by, for example, reacting a compound of the following formula [7]:

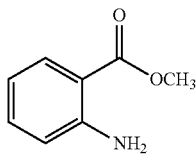

with a compound of the following formula [8]:

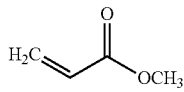

in the presence of a Lewis acid such as aluminum chloride to prepare a compound of the following formula [9]:

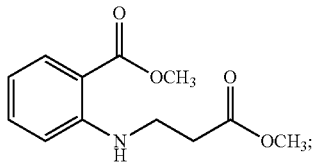

subjecting the compound [9] to intramolecular cyclization reaction in the presence of a base such as sodium methoxide in an appropriate solvent such as toluene, methanol or a mixture thereof to prepare a compound of the following formula [10]:

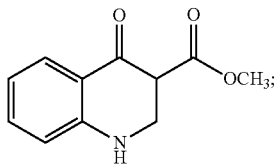

and subjecting the compound [10] to decarboxylation reaction in the presence of a base such as sodium hydroxide in an appropriate solvent such as toluene or a mixture of toluene and water.

Throughout the present specification, "lower alkyl group" means a $C_{1-6}$ alkyl group, "lower alkoxy group" means a $C_{1-6}$ alkoxy group, and "aryl group" means a 6- to 10-membered monocyclic or bicyclic aryl group.

Throughout the present specification, "halogen atom" means a fluorine atom, a chlorine atom, a bromine atom or an iodine atom etc., preferably a bromine atom.

The abbreviation in the present specification, unless otherwise defined, represents as follows:
Me: methyl
Et: ethyl
Ph: phenyl
tBu: tert-butyl
Ac: acetyl
THF: tetrahydrofuran
dppf: diphenylphosphioferrocene
PPh$_3$: triphenylphosphine
HPLC: High Performance Liquid Chromatography
Bn: benzyl
Ts: p-toluenesulfonyl
Ms: methanesulfonyl
TFA: trifluoroacetic acid
DPEN: 1,2-diphenylethylenediamine
DMSO: dimethylsulfoxide The following examples illustrate the embodiments of the present invention, but are not meant to limit the scope of the invention.

EXAMPLES

Example 1

(1) Step a: Preparation of a chlorobenzene monosolvate of 2,3-bis(methoxycarbonyl)-6,7-dimethoxy-1-[2-(4-oxo-1,2,3,4-tetrahydroquinolin-1-yl)-4-pyridyl]naphthalene

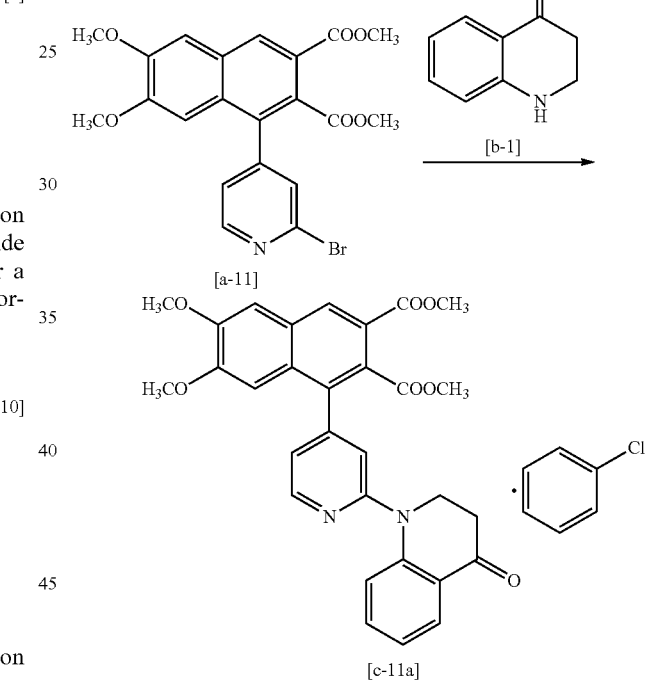

Toluene was put into a reaction vessel at room temperature and thereto was added water (2.50 mL) under stirring. The internal pressure of the vessel was reduced (−0.09 MPa) and maintained for five minutes, and thereto was charged nitrogen gas to restore the internal pressure. Thereto were added 1-(2-bromo-4-pyridyl)-2,3-bis(methoxycarbonyl)-6,7-dimethoxynaphthalene (20.0 g), 4-oxo-1,2,3,4-tetrahydroquinoline (6.71 g), cesium carbonate (42.5 g), palladium acetate (146 mg) and Xantphos (566 mg) at room temperature, followed by washing inside of the vessel with toluene (10 mL). The internal pressure of the vessel was reduced (−0.09 MPa) and maintained for five minutes, and thereto was charged nitrogen gas to restore the internal pressure (the procedure was carried out three times). The mixture was warmed to 45° C. to 65° C. under nitrogen stream and stirred at the same temperature for 17 hours. After cooling the reaction mixture (internal temperature: 40° C.), thereto was added dropwise water (200 mL) at the same temperature over a period of 10 minutes and the mixture was allowed to stand nearly for 30 minutes. Subsequently, thereto was added dropwise n-heptane (200 mL) at 40° C. (internal temperature) over a period of 10 minutes and the mixture was allowed to stand at the same temperature nearly for 30 minutes. After cooling the mixture (internal temperature: 10±5° C.), the mixture was allowed to stand at the same temperature nearly for 30 minutes. The precipitated solid materials were collected by filtration, washed with n-heptane (40.0 mL) and water (40.0 mL) and dried to moisture content of 3.0% or lower in a vacuum dryer (at 75° C. or lower) to obtain the captioned compound as a crude product. To the crude product was added chlorobenzene (400 mL) and the mixture was stirred under warming (internal temperature: 70±5° C.) nearly for 30 minutes. To the mixture was added magnesium sulfate (10.0 g) and the mixture was further stirred nearly for 30 minutes. To the mixture was added silica gel (10.0 g) and the mixture was stirred at the same temperature nearly for 30 minutes. To the mixture was added activated charcoal (2.00 g) and chlorobenzene (20 mL) and the mixture was stirred at the same temperature as above nearly for 30 minutes, followed by filtration while maintaining its internal temperature at 50° C. or more. The residue was washed with warmed chlorobenzene (70° C., 120 mL), and the washings and the filtrate were combined and concentrated to nearly one-seventh its volume in water bath at 75° C. After cooling the resultant residue (internal temperature: 30° C. or lower), thereto was added dropwise n-heptane (140 mL) at the same temperature over a period of 10 minutes, and after cooling thereof (internal temperature: 10±5° C.), the mixture was allowed to stand at the same temperature nearly for 30 minutes. The resultant crystals were collected by filtration, washed with a mixture of chlorobenzene (20 mL) and n-heptane (40 mL) which was cooled at 10±5° C., and dried in a vacuum dryer (55° C. or lower) to obtain the captioned compound [b-11a] (22.56 g) as yellow crystals (yield: 81%).

MS(APCI) m/z: 527[M+H]$^+$ $^1$H-NMR (CHCl$_3$-d): δ 2.76-2.95 (2H, m), 3.70 (3H, s), 3.82 (3H, s), 3.95 (3H, s), 4.03 (3H, s), 4.22-4.34 (1H, m), 4.57-4.62 (1H, m), 6.77 (1H, s), 6.96-6.99 (2H, m), 7.08-7.46 (9H, m), 7.98-8.00 (1H, dd), 8.48 (1H, s), 8.50-8.52 (1H, d)

M. p. 216-218° C.

Purity by HPLC area %: 99.62% (*1)

(*1) Conditions in HPLC:
Column: L-Column ODS (φ 4.6 mm×150 mm; manufactured by CERI)
Mobile phase A: water/acetonitrile/TFA (650:350:0.1)
Mobile phase B: acetonitrile/water/TFA (900:100:0.1)

(2) Step b: Preparation of acetonitrile monosolvate of 6,7-dimethoxy-1-[2-[(4S)-4-hydroxy-1,2,3,4-tetrahydroquinolin-1-yl]-4-pyridyl]-2,3-bis(methoxycarbonyl) naphthalene

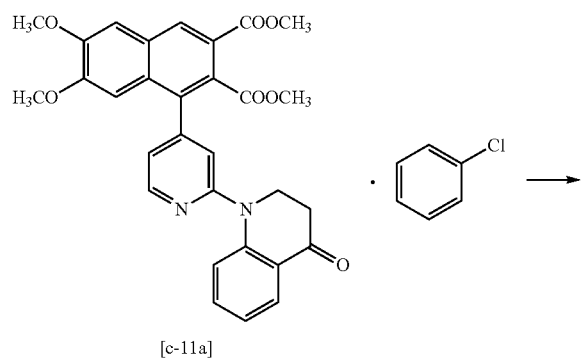

[c-11a]

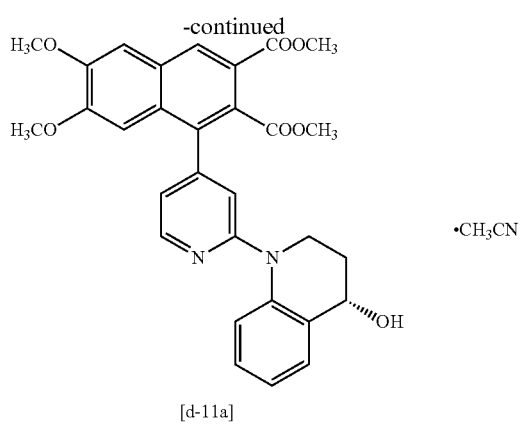

[d-11a]

To a reaction vessel (reaction vessel A) was added tetrahydrofuran (42.0 mL) under nitrogen stream and thereto was added dropwise formic acid (18.4 g) at an internal temperature of 30° C. or lower. To another reaction vessel (reaction vessel B) were added tetrahydrofuran (75.0 mL) and triethylamine (23.8 g) under nitrogen stream and thereto was added successively the compound obtained in the above step (1) (15.0 g) and chloro[(1S,2S)—N-(p-toluenesulfonyl)-1,2-diphenylethanediamine](p-cymene)ruthenium(II) [RuCl[(1S,2S)-TsDPEN](p-cymene)] (149 mg; Kanto Chemical Co., Inc.) under stirring. After warming the mixture to 50±5° C. (internal temperature), thereto was added dropwise the solution of formic acid in tetrahydrofuran in the reaction vessel A over a period of two hours. The mixture and the washings (3 mL of tetrahydrofuran) from the reaction vessel A were combined and the reaction was carried out at 50±5° C. (internal temperature) for 16 hours. After cooling the reaction mixture to 25° C., thereto was added dropwise an aqueous citric acid solution (27.09 g of anhydrous citric acid in 48.0 mL of water) at 30° C. or lower to adjust pH 4.5 to 5.0. The mixture was stirred at 25±5° C. nearly for one hour and allowed to stand for 10 minutes, and the organic layer was separated. To the organic layer was added an aqueous 5% sodium hydrogen carbonate solution (2.25 g of sodium hydrogen carbonate in 42.8 mL of water) and the mixture was stirred (washed) nearly for 5 minutes. Subsequently, after confirming pH of the aqueous layer being 7.5 to 8.0, thereto was added 20% saline (9.00 g of NaCl in 36.0 mL of water) at 25±5° C. and the mixture was stirred nearly for 10 minutes and allowed to stand nearly for 10 minutes. The organic layer was separated and thereto was added activated charcoal (1.50 g), and the mixture was stirred at 25±5° C. nearly for 30 minutes and filtered. The filtrate and the washings (15.0 mL of tetrahydrofuran and 60.0 mL of acetonitrile) were combined and concentrated nearly to one-fourth its volume in a water bath (internal temperature: 50° C. or lower). To the resultant residue was added acetonitrile (45.0 mL) and concentrated to nearly one-3.5$^{th}$ its volume in a water bath (internal temperature: 50° C. or lower). To the resultant residue was added acetonitrile (60.0 mL) at 30±5° C. (internal temperature) and the mixture was allowed to stand at the same temperature nearly for one hour. Subsequently, to the mixture was added dropwise water (60.0 mL) at 30±5° C. over a period of 10 minutes and the mixture was stirred at the same temperature for 15 minutes. After gradually cooling to 10±5° C., the mixture was allowed to stand at the same temperature nearly for one hour. The precipitated crystals were collected by filtration, washed with acetonitrile (15.0 mL) and dried in a vacuum dryer (at 55° C. or lower) to obtain the captioned compound (11.42 g) as pale yellow crystals (yield: 85%).

MS(APCI) m/z; 529 [M+H]$^+$ $^1$H-NMR (DMSO-d6): δ 1.79-1.91 (1H, m), 1.99-2.13 (4H, m), 3.50-3.61 (3H, d), 3.68-3.93 (10H, m), 4.03-4.10 (1H, m), 4.55-4.66 (1H, m), 5.37-5.39 (1H, dd), 6.70-6.88 (2H, m), 6.89-7.01 (2H, m), 7.04-7.15 (1H, m), 7.26-7.29 (1H, dd), 7.39-7.41 (1H, d), 7.69-7.71 (d, 1H), 8.40-8.41 (1H, d), 8.53 (1H, s)

M. p. 107-109° C.

Enantiomeric excess (purity by HPLC area %): 99.52% ee (*2)

(*2) Conditions in HPLC:
Column: CHIRALCEL OD-H (ϕ 4.6 mm×250 mm; manufactured by DAICEL Chemical Industry Co., Ltd.)
Mobile phase: Hexane/Ethanol (4:1)

(3) Step c: Preparation of a 3/2 hydrate of 6,7-dimethoxy-1-[2-[(4S)-4-hydroxy-1,2,3,4-tetrahydroquinolin-1-yl]-4-pyridyl]-2,3-bis(hydroxymethyl)naphthalene

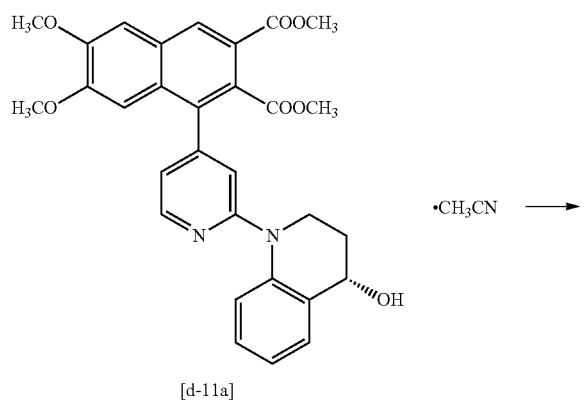

[d-11a]

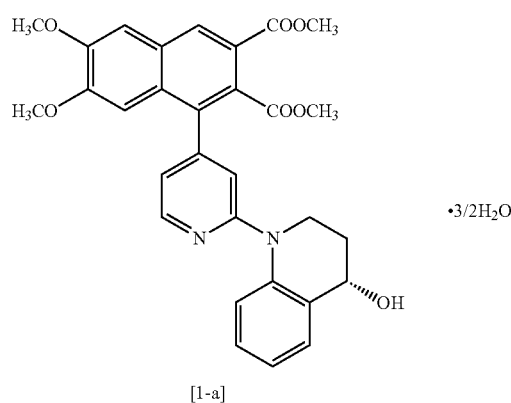

[1-a]

The compound (10.0 g) obtained in the above step (2) was dissolved in tetrahydrofuran (100 mL) under stirring and thereto was added sodium borohydride (3.99 g) at room temperature. After warming the mixture to 45±5° C., thereto was added dropwise methanol (6.41 mL) over a period of one hour and the mixture was stirred at the same temperature for one hour. To the reaction mixture was further added dropwise methanol (6.61 mL) over a period of one hour and the mixture was stirred at 45±5° C. for 14 hours. After cooling the reaction mixture (internal temperature: 30° C. or lower), thereto was added dropwise acetone (7.74 mL). The mixture was added dropwise to water (100 mL) at 30° C. or lower and the mixture was washed successively with tetrahydrofuran (5.0 mL) and water (5.0 mL). Subsequently, the solution was stirred at 40±5° C. for 10 minutes and allowed to stand nearly for 10 minutes. To the organic layer was added water (50 mL) and NaCl (15 g) and the mixture was stirred at 40±5° C. for 10 minutes and allowed to stand nearly for 10 minutes. The organic layer was separated and concentrated to nearly one-fourth its volume in a water bath (at 55° C. or lower) and to the residue was added ethanol (20.0 mL) and warmed to 50±5° C. to dissolve it. The solution was filtered by a filter pre-coated with activated charcoal (1.00 g) at 50±5° C. The filtrate and the washings (10.0 mL of warmed ethanol) were combined and thereto was added dropwise purified water (60.0 mL) at 50±5° C. over a period of one hour and the mixture was stirred at the same temperature for 15 minutes. Thereto was added dropwise purified water (10.0 mL) at 50±5° C. over a period of 10 minutes and the mixture was stirred at the same temperature for one hour. After gradually cooling to 5±5° C., the mixture was allowed to stand at the same temperature nearly for 30 minutes. The mixture was filtered and the residue (precipitated crystals) was washed twice with a mixture of ethanol and purified water (3.00 mL/7.00 mL) which was cooled to 5±5° C. and dried in a vacuum dryer (40±5° C.) to obtain the captioned compound (8.07 g) as colorless crystals (yield: 92%).

MS(APCI) m/z; 473 [M+H]$^+$ $^1$H-NMR (DMSO-d6): δ 1.80-1.90 (1H, m), 2.01-2.1 (1H, m), 3.60-3.66 (3H, d), 3.77-3.89 (4H, m), 3.99-4.14 (1H, m), 4.26-4.44 (2H, m), 4.59-4.63 (1H, m), 4.76-4.86 (3H, m), 5.24-5.29 (1H, m), 5.34-5.37 (1H, m), 6.59-6.65 (1H, d), 6.85-6.90 (2H, m), 7.00-7.06 (2H, m), 7.32-7.39 (3H, m), 7.87 (1H, s), 8.41-8.42 (1H, d)

Water content: 5.3% (Coulometric titration method)

Enantiomeric excess (purity by HPLC area %): 99.34% ee (*3)

(*3) Conditions in HPLC:
Column: CHIRALCEL OJ-H (ϕ 4.6 mm×250 mm; manufactured by DAICEL Chemical Industry Co., Ltd.)
Mobile phase: Hexane/Ethanol (4:1)

Examples 2 to 7

The compound [c-11] was prepared in accordance with the condition for reaction described in the following Tables 1 and 2. Meanwhile, the amount of each starting material etc. in Tables 1 and 2 is represented by mol % (molar equivalent, or v/w) thereof to the compound [a-11]. The yield of the compound [c-11] is represented by area % value in HPLC carried out in the following condition (*4).

(*4) Conditions in HPLC:
Column: L-Column ODS (ϕ 4.6 mm×150 mm; manufactured by CERI)
Mobile phase A: water/acetonitrile/TFA (900:100:1)
Mobile phase B: acetonitrile/water/TFA (900:100:1)

TABLE 1

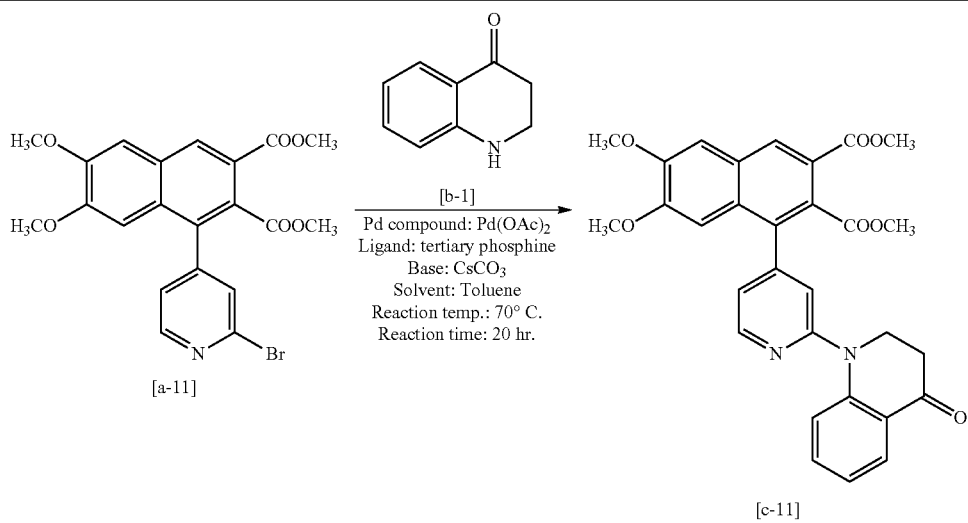

|  | Ex. 2 | Ex. 3 | Ex. 4 |
|---|---|---|---|
| Amount of Pd(OAc)$_2$ (mol %) |  | 15 |  |
| Ligand   Tertiary phosphine | Ligand-1 | BIPHEP | Cl—MeO—BIPHEP |
| Amount (mol %) |  | 22.5 |  |
| Amount of Base (molar equivalent) |  | 3.0 |  |
| Amount of Solvent (v/w) |  | 20 |  |
| Amount of Compound [b-1] (molar equivalent) |  | 1.1 |  |
| Yield of Compound [c-11] (HPLC area %) | 66.6 | 75.8 | 77.6 |

*: "Amount" is represented by a ratio to Compound [a-11].

TABLE 2

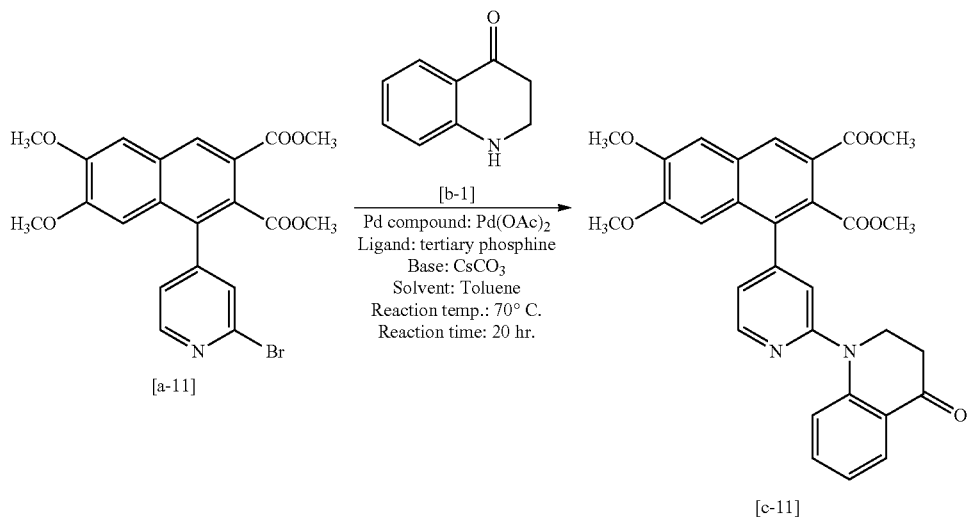 [SMILES: COC(=O)c1cc2cc(OC)c(OC)cc2c(-c2ccnc(Br)c2)c1C(=O)OC ; O=C1CCNc2ccccc21 ; COC(=O)c1cc2cc(OC)c(OC)cc2c(-c2ccnc(N3CCC(=O)c4ccccc43)c2)c1C(=O)OC]

|  | Ex. 5 | Ex. 6 | Ex. 7 |
|---|---|---|---|
| Amount of Pd(OAc)$_2$ (mol %) |  | 15 |  |
| Ligand   Tertiary phosphine | D$^t$BPF | Xantphos | Dave-Phos |
| Amount (mol %) |  | 22.5 |  |
| Amount of Base (molar equivalent) |  | 3.0 |  |
| Amount of Solvent (v/w) |  | 20 |  |
| Amount of Compound [b-1] (molar equivalent) |  | 1.1 |  |
| Yield of Compound [c-11] (HPLC area %) | 65.4 | 66.8 | 54.6 |

*: "Amount" is represented by a ratio to Compound [a-11].

Examples 8 to 13

The compound [d-11a] was prepared in accordance with the condition for reaction described in the following Tables 3 and 4. Meanwhile, the amount of each starting material etc. in Tables 3 and 4 is represented by mol % (M or v/w) thereof to the compound [c-11a]. The enantiomeric excess of the compound [d-11a] is represented by area % value in HPLC carried out in the following condition (*5). Meanwhile, the catalyst used in each example is shown as follows.

Catalyst a

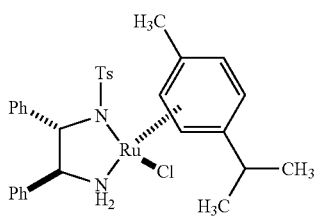

Catalyst b

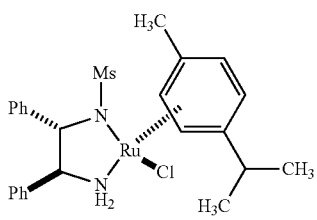

Catalyst c

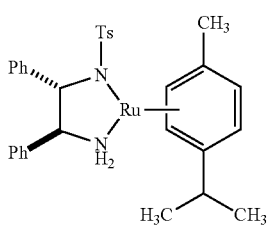

(*5) Conditions in HPLC:
Column: CHIRALCEL OD-H (φ 4.6 mm×250 mm; manufactured by DAICEL Chemical Industry Co., Ltd.)
Mobile phase: Hexane/Ethanol (4:1)

TABLE 3

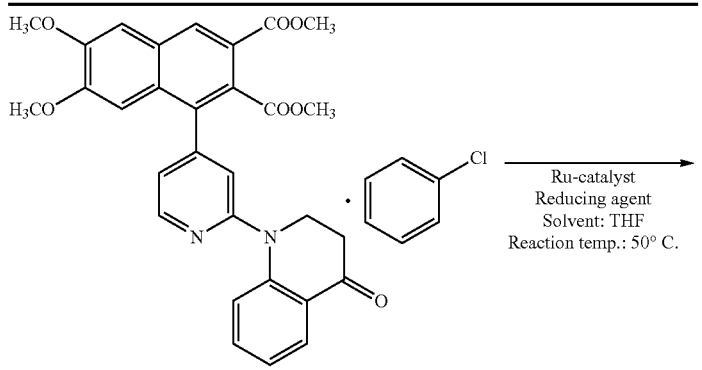

[c-11a]

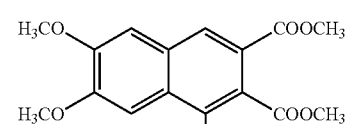

[d-11a]

| | Ex. 8 | Ex. 9 | Ex. 10 |
|---|---|---|---|
| Ru-catalyst/Amount (mol %) | Catalyst a/2 | Catalyst b/2 | Catalyst c/2 |
| Reducing agent/Amount (M) | Azeotropic mixture of formic acid and triethylamine (5:2)/2 | | |
| Amount of Solvent (v/w) | 10 | | |
| Reaction time (h) | 22 | 15 | 15 |
| Enantiomeric excess of Compound [d-11a] (HPLC area %): % ee | 99.52 | 99.26 | 99.26 |

*: "Amount" is represented by a ratio to 1 g of Compound [c-11a].

TABLE 4

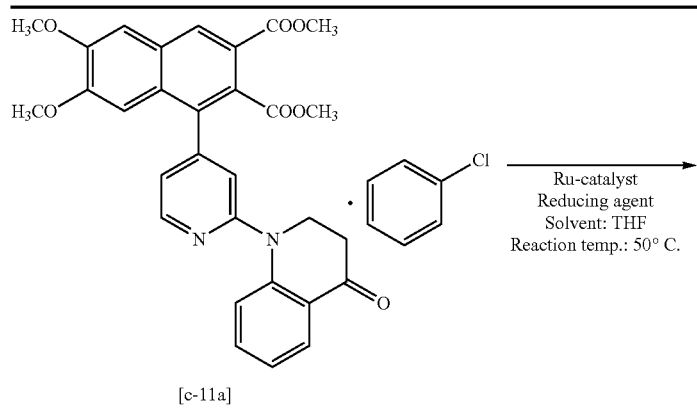

[c-11a]

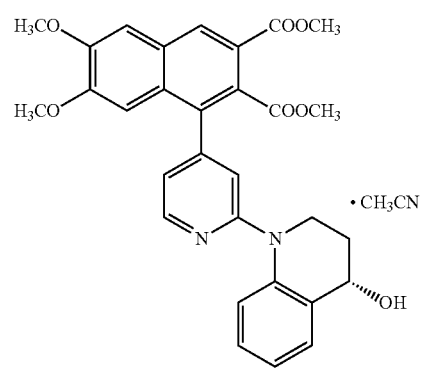

[d-11a]

| | Ex. 11 | Ex. 12 | Ex. 13 |
|---|---|---|---|
| Ru-catalyst/Amount (mol %) | Catalyst a/2 | Catalyst b/2 | Catalyst c/2 |
| Reducing agent/Amount (M) | A mixture of 88% formic acid and >99% triethylamine (5:2)/2 | | |
| Amount of Solvent (v/w) | 10 | | |
| Reaction time (h) | 15 | 15 | 15 |
| Enantiomeric excess of Compound [d-11a] (HPLC area %): % ee | 99.28 | 99.44 | 99.34 |

*: "Amount" is represented by a ratio to 1 g of Compound [c-11a].

Examples 14 to 16

The compound [I-a] was prepared in accordance with the condition for reaction described in the following Table 5. Meanwhile, the amount of each starting material etc. in Table 5 is represented by mol % (M or v/w) thereof to the compound [d-11a]. The yield of the compound [I-a] is represented by area % value in HPLC carried out in the following condition (*6).

(*6) Conditions in HPLC:
  Column: L-Column ODS (φ 4.6 mm×150 mm; manufactured by CERI)
  Mobile phase A: water/acetonitrile/TFA (900:100:1)
  Mobile phase B: acetonitrile/water/TFA (900:100:1)

TABLE 5

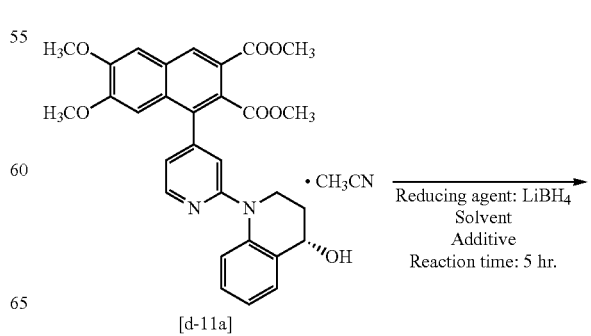

[d-11a]

TABLE 5-continued

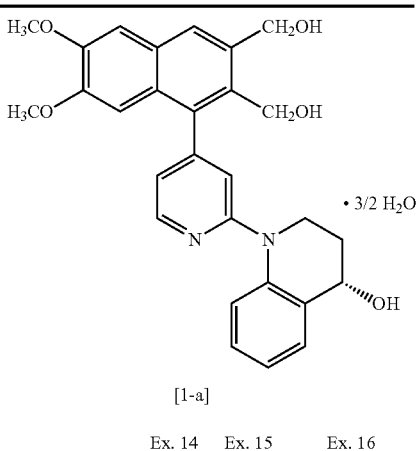

[1-a]

| | Ex. 14 | Ex. 15 | Ex. 16 |
|---|---|---|---|
| Amount of Reducing agent (molar equivalent) | 4 | 7 | 7 |

TABLE 5-continued

| Solvent/Amount (v/w) | THF/10 | THF/10 | THF + Toluene/ 5 + 5 |
|---|---|---|---|
| Additive/Amount (molar equivalent) | MeOH/8 | — | — |
| Reaction temperature (° C.) | 65 | 65 | 100 |
| Yield of Compound [I-a] (HPLC area %) | 94.36 | 94.96 | 88.90 |

*: "Amount" is represented by a ratio to Compound [d-11a].

Examples 17 to 21

The compound [d-11a] was prepared in accordance with the condition for reaction described in the following Tables 6 and 7. Meanwhile, the amount of each starting material etc. in Tables 6 and 7 is represented by mol % (M or v/w) thereof to the compound [c-11a]. The enantiomeric excess of the compound [d-11a] is represented by area % value in HPLC carried out in the following condition (*7).

(*7) Conditions in HPLC:
  Column: CHIRALCEL OD (φ 4.6 mm×250 mm; manufactured by DAICEL Chemical Industry Co., Ltd.)
  Mobile phase: Hexane/Ethanol (5:2)

TABLE 6

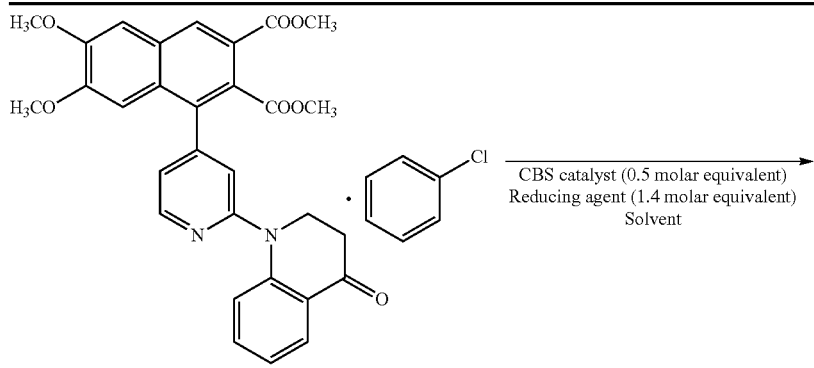

[c-11a]

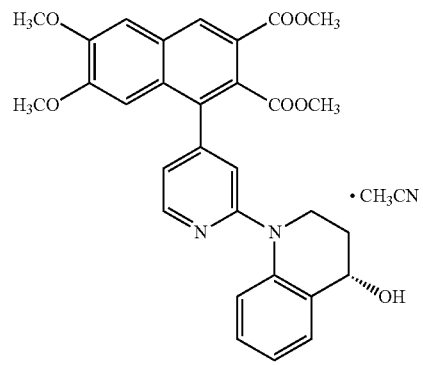

[d-11a]

TABLE 6-continued

|  | Ex. 17 | Ex. 18 | Ex. 19 |
|---|---|---|---|
| CBS catalyst | 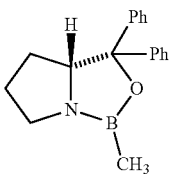 | | |
| | [R-CBS1] | | |
| Reducing agent | $BH_3$—$SMe_2$ complex | $BH_3$—THF complex | $BH_3$—THF complex |
| Solvent/Amount (v/w) | Dichloromethane/20 | | THF/35 |
| Reaction temperature (° C.) | | 0 | |
| Reaction time (h) | | 4 | |
| Enantiomeric excess of Compound [d-11a] (HPLC area %): % ee | 98.10 | 98.40 | 97.90 |

*: "Amount" is represented by a ratio to Compound [c-11a].

TABLE 7

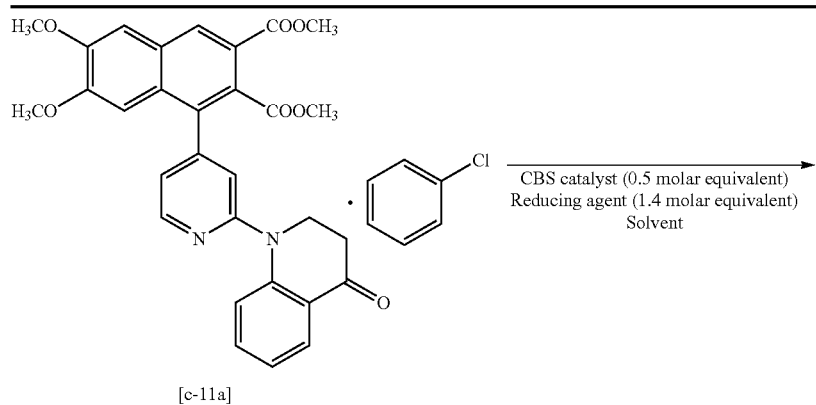

[c-11a]

$\xrightarrow{\text{CBS catalyst (0.5 molar equivalent)} \atop \text{Reducing agent (1.4 molar equivalent)} \atop \text{Solvent}}$

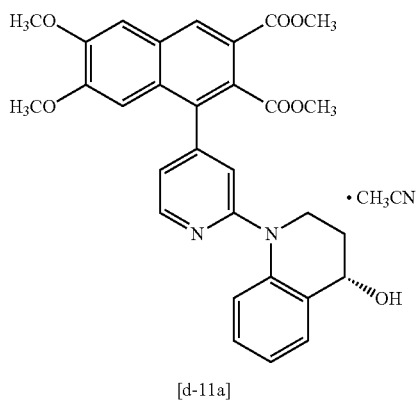

[d-11a]

TABLE 7-continued

|  | Ex. 20 | Ex. 21 |
| --- | --- | --- |
| CBS catalyst | 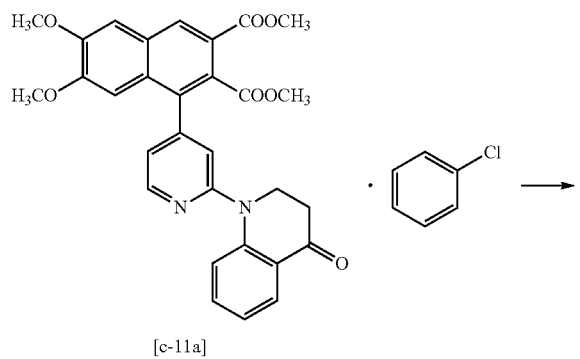 [R-CBS1] | |
| Reducing agent | BH$_3$-diethylaniline complex | |
| Solvent/Amount (v/w) | THF/35 | |
| Reaction temperature (° C.) | 22 | 40 |
| Reaction time (h) | | 1.5 |
| Enantiomeric excess of Compound [d-11a] (HPLC area %): % ee | 98.28 | 94.78 |

*: "Amount" is represented by a ratio to Compound [c-11a].

Example 22

Preparation of acetonitrile monosolvate of 6,7-dimethoxy-1-[2-[(4S)-4-hydroxy-1,2,3,4-tetrahydroquinolin-1-yl]-4-pyridyl]-2,3-bis(methoxycarbonyl)naphthalene

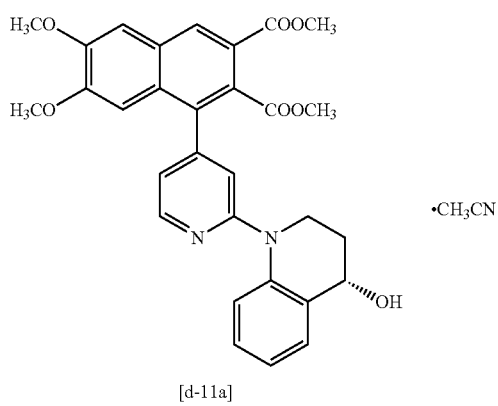

To a reaction vessel were added the compound [c-11a] (15.0 g), potassium formate (4.94 g), chlorobenzene (45.0 mL) and methanol (30.0 mL) and argon- or nitrogen-replacement was carried out under stirring the mixture at room temperature. To the mixture was added RuCl[(1S,2S)—BnSO$_2$DPEN](p-cymene) (14.932 mg; Kanto Chemical Co., Inc.) and argon- or G3 nitrogen-replacement was carried out under stirring the mixture at room temperature. The reaction vessel was warmed to 50° C. in a water bath and the mixture was stirred for 24 hours (300 rpm). After cooling the reaction mixture to 25° C. or lower, thereto were added chlorobenzene (100 mL) and water (50 mL) and the organic layer was separated. The organic layer was washed successively with water (50 mL×2) and a saturated saline (50 mL), dried over anhydrous sodium sulfate (10.00 g) and filtered. The filtrate was concentrated at 40° C. to 4.5 v/w and the residue was stirred at room temperature for 15 hours and allowed to stand at 0° C. for 4.5 hours. The precipitated crystals were collected by filtration, washed with cold chlorobenzene (15 mL) and dried in vacuo at room temperature to obtain the captioned compound as a crude product (yield: 97.3%). To a solution of the product in THF (112 mL) was added activated charcoal (1.50 g) and the mixture was stirred at 25±5° C. for 30 minutes or more and filtered. The insoluble materials (unfiltered residue) were washed successively with THF (14.0 mL) and acetonitrile (56.0 mL). The washings and the filtrate were combined and concentrated to 4.5 v/w to 3.5 v/w (external temperature: 50° C. or lower). To the residue was added acetonitrile (42.0 mL) and the mixture was concentrated to 4.0 v/w to 3.0 v/w (external temperature: 50° C. or lower). To the residue was further added acetonitrile (42.0 mL) and the mixture was concentrated to 4.0 v/w to 3.0 v/w (external temperature: 50° C. or lower). Thereto was added acetonitrile (56.0 mL) at 30±5° C. (internal temperature) and allowed to stand at the same temperature over a period of one hour from the beginning of crystallization. To the mixture was added dropwise water (56.0 mL) at 30±5° C. over a period of 10 minutes and the mixture was stirred at the same temperature for 15 minutes. After gradually cooling to 10±5° C., the mixture was allowed to stand at the same temperature over a period of one hour. The precipitated crystals were collected by filtration, washed with a cold acetonitrile (15.0 mL, 10±5° C.) and dried in a vacuum dryer at 55° C. or lower to obtain the captioned compound [d-11a] (12.07 g) as crystals (yield: 90.3%).

Enantiomeric excess (purity by HPLC area %): 99.71% ee (*8)

(*8) Conditions in HPLC:

Column: CHIRALCEL OD-H (φ 4.6 mm×250 mm; manufactured by DAICEL Chemical Industry Co., Ltd.)

Mobile phase: Hexane/Ethanol (4:1)

Example 23

Step a

Preparation of 2,3-bis(methoxycarbonyl)-6,7-dimethoxy-1-[2-(4-oxo-1,2,3,4-tetrahydroquinolin-1-yl)-4-pyridyl]naphthalene (free form)

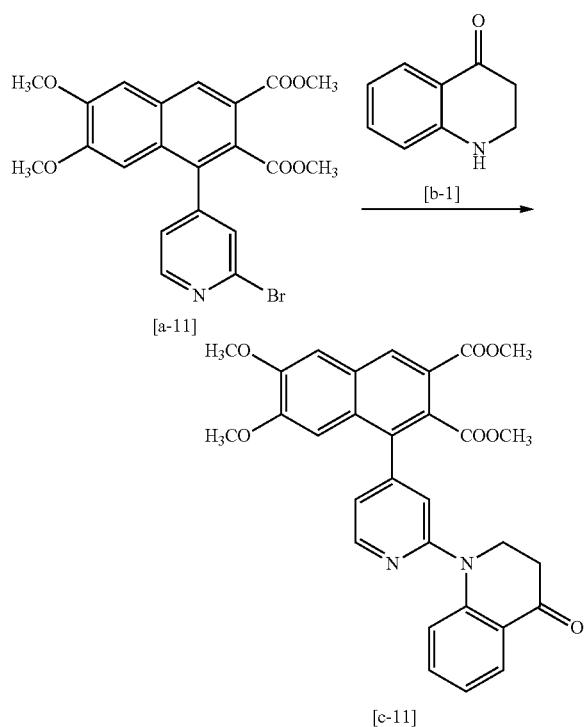

The internal pressure of a reaction vessel was reduced (−0.09 MPa or less) and thereto was charged nitrogen gas and added toluene (120 mL) at room temperature and then added tripotassium phosphate (41.51 g) under stirring. After cooling the mixture (internal temperature: 20° C. or lower), thereto was added sodium sulfate decahydrate (13.425 g) at the same temperature. To the mixture were added 1-(2-bromo-4-pyridyl)-2,3-bis(methoxycarbonyl)-6,7-dimethoxynaphthalene (30.0 g), 4-oxo-1,2,3,4-tetrahydroquinoline (10.07 g), palladium acetate (219 mg) and Xantphos (849 mg), and the inside of the vessel was washed with toluene (15 mL). The internal pressure of the vessel was reduced (−0.09 MPa) and maintained for 5 minutes, and then nitrogen gas was charged thereto to restore the internal pressure (the procedure was carried out three times). The mixture was warmed to 45° C. to 65° C. under nitrogen stream and stirred at the same temperature for 15 hours. In the course of reaction, the internal temperature was maintained at about 47° C. over the initial 10 hours and, after that, maintained at about 57° C. After cooling the reaction mixture (internal temperature: 40° C.), thereto was added dropwise an aqueous citric acid solution (25.04 g of citric acid in 120 mL of water) at the same temperature, and thereto was added dropwise chloroform (150 mL). After warming the mixture at 45±5° C. (internal temperature), the mixture was filtered through Celite at 20° C. or more. The organic layer was separated from the filtrate and to the filtrate was added water (90 mL) at 20° C. or more and the mixture was stirred nearly for 10 minutes. The organic layer was separated and concentrated in vacuo at 60° C. or lower and to the residue was added toluene (90 mL) and the mixture was concentrated in vacuo at 60° C. or lower. The residue was allowed to stand at 20±5° C. or lower (internal temperature) nearly for one hour and the precipitated crystals were collected by filtration. The crystals were washed with a cold methanol (5±5° C., 60 mL) to obtain a toluene monosolvate of the captioned compound [c-11] as crystals. To the crystals was added a mixture of chloroform (60 mL) and methanol (6 mL) at 30±5° C. and the mixture was stirred nearly for 15 minutes. Thereto was added dropwise methanol (54 mL) at 15±5° C. over a period of one hour and the mixture was stirred at the same temperature for one hour. Subsequently, to the mixture was added methanol (39 mL) and the mixture was cooled to 5±5° C. and stirred at the same temperature for one hour. The precipitated crystals (a chloroform monosolvate of the captioned compound [c-11]) were collected by filtration, washed with a cold methanol (5±5° C., 90 mL) and dried in vacuo at 60° C. or lower to obtain the captioned compound (free form, 34.3 g) as pale yellow crystals (yield: 86%).

Purity: 99.4% (HPLC area %) (*9)

(*9) Conditions in HPLC:

Column: L-Column ODS (φ 4.6 mm×150 mm; manufactured by CERI)

Mobile phase A: water/acetonitrile/TFA (650:350:0.1)

Mobile phase B: acetonitrile/water/TFA (900:100:0.1)

Example 24

Step b

Preparation of acetonitrile monosolvate of 6,7-dimethoxy-1-[2-[(4S)-4-hydroxy-1,2,3,4-tetrahydroquinolin-1-yl]-4-pyridyl]-2,3-bis(methoxycarbonyl)naphthalene

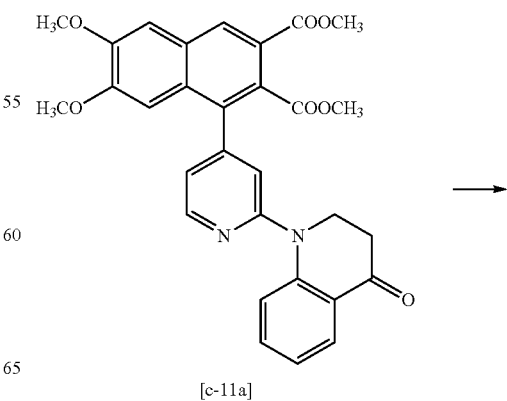

-continued

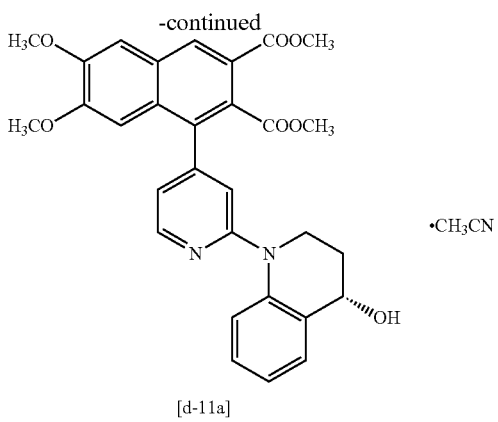

[d-11a]

To a reaction vessel (reaction vessel A) was added tetrahydrofuran (42.0 mL) under inert gas stream and thereto was added dropwise 88% formic acid (18.5 g) at an internal temperature at 30° C. or lower. To a reaction vessel (reaction vessel B) were added tetrahydrofuran (75.0 mL) and triethylamine (23.8 g) under inert gas stream and thereto were added successively the compound obtained in the above EXAMPLE 23 (12.4 g) and RuCl[(1S,2S)-TsDPEN](p-cymene) (150 mg) under stirring. The internal pressure of the vessel was reduced (−0.09 MPa) and then nitrogen gas was charged thereto to restore the internal pressure (the procedure was carried out three times). After warming the mixture in the reaction vessel B to 50±5° C. (internal temperature), thereto was added dropwise the mixture of tetrahydrofuran/formic acid in the reaction vessel A at the same temperature over a period of two hours. The reaction vessel A was washed with tetrahydrofuran (2.98 mL) and the washings were added to the reaction vessel B. The mixture was stirred under warming 50±5° C. (internal temperature) nearly for 16 hours. After cooling the reaction mixture to 25° C. or lower, thereto was added dropwise an aqueous citric acid solution (27.1 g of anhydrous citric acid in 48.0 mL of water) at 30° C. or lower to adjust pH 4.5 to 5.0 in the aqueous layer. The mixture was stirred at 25±5° C. nearly for one hour and allowed to stand nearly for 10 minutes. The organic layer was separated and thereto was added an aqueous sodium hydrogen carbonate solution (2.23 g of sodium hydrogen carbonate in 42.8 mL of water) at 25±5° C. and the mixture was stirred nearly for 10 minutes. After adjusting pH in the aqueous layer within 7.5 to 8.0, the mixture was allowed to stand nearly for 10 minutes and the organic layer was separated. To the organic layer was added a saline (9.05 g of NaCl in 36.0 mL of water) at 25±5° C. and the mixture was stirred nearly for 10 minutes and allowed to stand nearly for 10 minutes. The organic layer was separated and thereto was added activated charcoal (1.49 g), and the mixture was stirred at 25±5° C. nearly for 30 minutes and filtered. The unfiltered residue was washed successively with tetrahydrofuran (15.0 mL) and acetonitrile (60.0 mL) and the filtrate and the washings were combined and concentrated (at an external temperature of 50° C. or lower). To the resultant residue was added acetonitrile (45.0 mL) and concentrated (external temperature at 50° C. or lower). To the resultant residue was added acetonitrile (45.0 mL) and concentrated (at an external temperature of 50° C. or lower). To the resultant residue was added acetonitrile (60.0 mL) at 30±5° C. (internal temperature) and the mixture was allowed to stand at the same temperature nearly for one hour. To the mixture was added dropwise water (60.0 mL) at 30±5° C. over a period of 10 minutes. The mixture was stirred at 30±5° C. for 15 minutes. After gradually cooling to 10±5° C., the mixture was allowed to stand at the same temperature nearly for one hour. The precipitated crystals were collected by filtration, washed with cold acetonitrile (10±5° C., 15.0 mL) and dried in a vacuum dryer (at 55° C. or lower) to obtain the captioned compound (12.4 g) as pale yellow crystals (yield: 92.8%).

Purity: 99.65% (purity by HPLC area %) (*10)
(*10) Conditions in HPLC:
  Column: L-Column ODS (φ 4.6 mm×150 mm; manufactured by CERI)
  Mobile phase A: water/acetonitrile/TFA (900:100:1)
  Mobile phase B: acetonitrile/water/TFA (900:100:1)
Enantiomeric excess (Purity by HPLC area %): 99.54% ee (*11)
(*11) Conditions in HPLC:
  Column: CHIRALCEL OD-H (φ 4.6 mm×250 mm; manufactured by DAICEL Chemical Industry Co., Ltd.)
  Mobile phase: Hexane/Ethanol (4:1)

INDUSTRIAL APPLICABILITY

The above-obtained compound [I] shows a selective PDE4-inhibitory activity, thereby is useful as a medicament such as a dermatitis-treating agent, a skin lesion-treating agent, an anti-itching agent and the like. The method of the present invention can be an industrially advantageous method of producing the compound [I] useful as a medicament.

The invention claimed is:
1. A method of producing an optically active naphthalene compound of the following formula [I]:

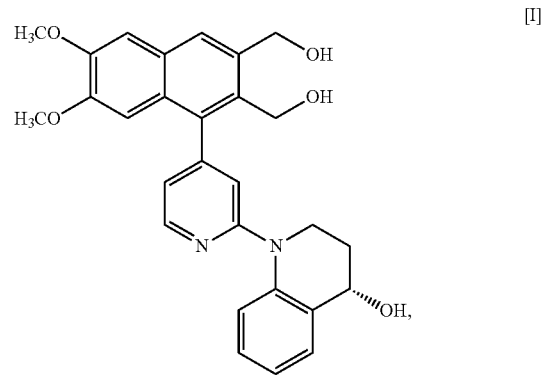 [SMILES: COc1cc2cc(CO)c(CO)c(-c3ccnc(N4CC[C@H](O)c5ccccc54)c3)c2cc1OC]

which comprises the following steps of:
(step a) reacting a compound of the following formula [a-1]:

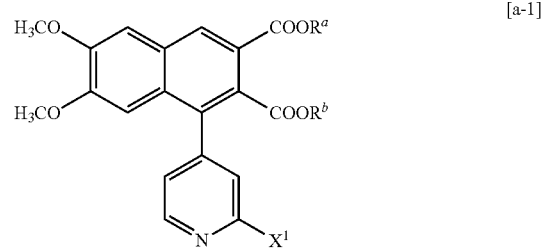

wherein $R^a$ and $R^b$ are the same or different and each of them is a lower alkyl group and $X^1$ is a halogen atom with a compound of the following formula [b-1]:

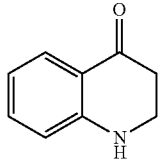

[b-1]

in the presence of a catalyst comprising a palladium compound and a tertiary phosphine ligand and a base and in the presence or absence of water or a water-donating substance to produce a compound of the following formula [c-1]:

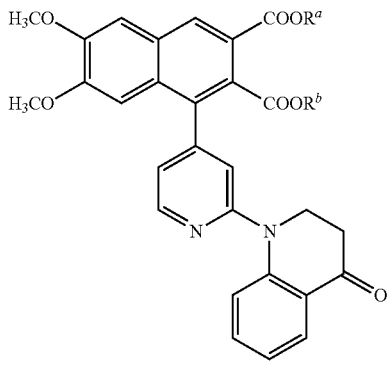

[c-1]

wherein the symbols are the same as defined above,
or a solvate thereof,
(step b) subjecting the above compound [c-1] or a solvate thereof to
(A) an asymmetric hydrogenation in the presence of a ruthenium complex (a chiral ruthenium catalyst) prepared from a ruthenium compound and a chiral ligand and a hydrogen donor and in the presence or absence of a base, or
(B) an asymmetric hydrogenation in the presence of an optically active oxazaborolidine compound (CBS catalyst) of the following formula [R-CBS]:

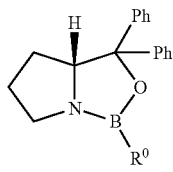

[R-CBS]

wherein Ph represents a phenyl group and $R^0$ is a lower alkyl group or a phenyl group and a boron hydride compound to produce a compound of the following formula [d-1]:

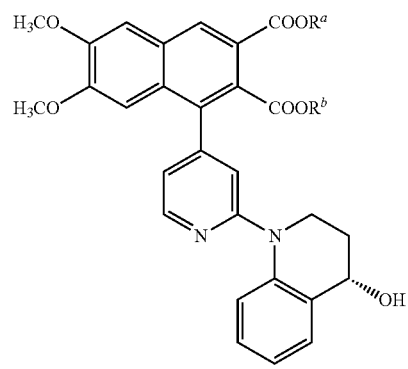

[d-1]

wherein the symbols are the same as defined above,
or a solvate thereof, and
(step c) treating the above compound [d-1] or a solvate thereof with a reducing agent.

2. The method according to claim 1 in which the water-donating substance in the step a is sodium sulfate decahydrate or a hydrated zeolite.

3. The method according to claim 1 in which the asymmetric hydrogenation in the step b is carried out in the presence of a ruthenium complex (a chiral ruthenium catalyst) prepared from a ruthenium compound and a chiral ligand and a hydrogen donor and in the presence or absence of a base.

4. The method according to claim 1 in which the asymmetric hydrogenation in the step b is carried out in the presence of an optically active oxazaborolidine compound [R-CBS] and a boron hydride compound.

5. The method according to claim 3 in which, in the step a, the palladium compound is palladium acetate, the tertiary phosphine ligand is a monodentate or bidentate phosphine ligand of the following formula [L-1]:

$(R^{01})_2P-Q-R^{02}$  [L-1]

wherein $R^{01}$ represents a phenyl group, a tert-butyl group or a cyclohexyl group, Q represents (a) a phenylene group, (b) a biphenylene group optionally substituted by a group selected from the group consisting of a halogen atom and a methoxy group, (c) a ferrocenyl group or (d) a 9,9-dimethylxanthenyl group and $R^{02}$ represents a diphenylphosphino group, a di-tert-butyl-phosphino group or a dimethylamino group
and the base is potassium carbonate, cesium carbonate or potassium phosphate,
in the step b, the ruthenium complex prepared from a ruthenium compound and a chiral ligand is a ruthenium-arene complex prepared from a ruthenium compound selected from the group consisting of: tetrachlorobis(benzene)diruthenium ([RuCl$_2$(C$_6$H$_6$)]$_2$), tetrachlorobis(p-cymene)diruthenium ([RuCl$_2$(C$_{10}$H$_{14}$)]$_2$), tetrachlorobis(hexamethyl benzene) diruthenium ([RuCl$_2$(C$_{12}$H$_{18}$)]$_2$), tetrachlorobis(mesitylene)diruthenium ([RuCl$_2$(C$_9$H$_{12}$)]$_2$), tetrachlorobis(ethyl benzoate)diruthenium ([RuCl$_2$(C$_9$H$_{10}$O$_2$)]$_2$), tetrabromobis(benzene)diruthenium ([RuBr$_2$(C$_6$H$_6$)]$_2$), tetrabromobis(p-cymene)diruthenium ([RuBr$_2$(C$_{10}$H$_{14}$)]$_2$), tetrabromobis(mesitylene)diruthenium ([RuBr$_2$(C$_9$H$_{12}$)]$_2$), tetraiodobis (benzene)diruthenium ([RuI$_2$(C$_6$H$_6$)]$_2$), tetraiodobis (p-cymene)diruthenium ([RuI$_2$(C$_{10}$H$_{14}$)]$_2$) and tetraiodobis(mesitylene)diruthenium ([RuI$_2$(C$_9$H$_{12}$)]$_2$), and an optically active ethylenediamine compound of the following formula [A]:

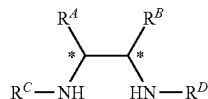

[A]

wherein R$^A$ and R$^B$ are each independently a lower alkyl group optionally having a substituent(s), an aryl group optionally having a substituent(s) or an aromatic heterocyclic group optionally having a substituent(s), or both of them combine together to form a cyclic group, R$^C$ and R$^D$ are each independently a hydrogen atom, a lower alkyl group optionally having a substituent(s), an acyl group, a carbamoyl group optionally having a substituent(s), a thioacyl group, a thiocarbamoyl group optionally having a substituent(s), a lower alkylsulfonyl group optionally having a substituent(s), an aryl-lower alkylsulfonyl group optionally having a substituent(s) or an arylsulfonyl group optionally having a substituent(s), and asterisk (*) represents an asymmetric carbon atom, the hydrogen donor is one or more compounds selected from the group consisting of an alcohol and a formic acid compound and the base is a tertiary amine, and in the step c, the reducing agent is a boron hydride compound.

6. The method according to claim 5 in which the tertiary phosphine ligand is 1,2-bis(diphenylphosphino)benzene, 2,2'-bis(diphenylphosphino)biphenyl, 2,2'-bis(diphenylphosphino)-5,5'-dichloro-6,6'-dimethoxy-1,1'-biphenyl (Cl-MeO-BIPHEP), 1,1'-bis(di-tert-butyl-phosphino)ferrocene, 4,5-bis(diphenylphosphino)-9,9-dimethylxanthene or 2-(dicyclohexylphosphino)-2'-(dimethylamino)biphenyl.

7. The method according to claim 5 in which the optically active ethylenediamine compound is a compound of the following formula [A-1]:

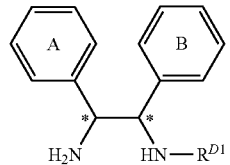

[A-1]

wherein ring A and ring B represent each independently a benzene ring optionally substituted by one to five groups selected from the group consisting of a lower alkyl group, a halogen atom and a lower alkoxy group and R$^{D1}$ represents a lower alkylsulfonyl group, a phenyl-lower alkylsulfonyl group or a lower alkylphenylsulfonyl group and the other symbols are the same as defined above.

8. The method according to claim 7 in which the optically active ethylenediamine compound is (S,S)—N-tosyl-1,2-diphenylethylenediamine, (S,S)—N-mesyl-1,2-diphenylethylenediamine, (S,S)—N-methyl-N'-tosyl-1,2-diphenylethylenediamine, (S,S)—N-p-methoxyphenylsulfonyl-1,2-diphenylethylenediamine, (S,S)—N-p-chlorophenylsulfonyl-1,2-diphenylethylenediamine, (S,S)—N-p-mesitylsulfonyl-1,2-diphenylethylenediamine, (S,S)—N-benzylsulfonyl-1,2-diphenylethylenediamine or (S,S)—N-(2,4,6-triisopropyl phenyl)sulfonyl-1,2-diphenylethylenediamine.

9. The method according to claim 3 in which the ruthenium complex prepared from a ruthenium compound and a chiral ligand is a ruthenium-arene complex of the following formula:

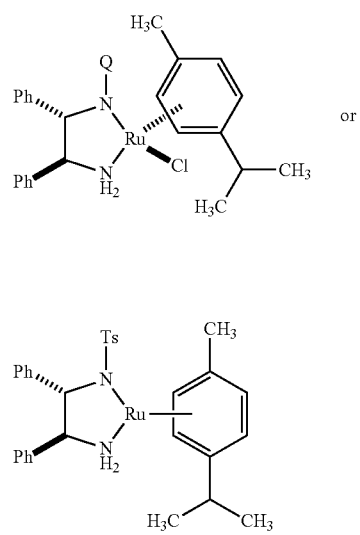

or wherein Ph represents a phenyl group, Q represents a methanesulfonyl group, a p-toluenesulfonyl group or a benzylsulfonyl group and Ts represents a p-toluenesulfonyl group.

10. The method according to claim 3 in which the ruthenium complex prepared from a ruthenium compound and a chiral ligand is a ruthenium-arene complex of the following formula:

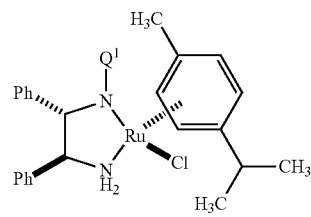

wherein Ph represents a phenyl group and Q$^1$ represents a p-toluenesulfonyl group or a benzylsulfonyl group.

11. The method according to claim 3 in which the palladium compound, the tertiary phosphine ligand and the base in the step a are respectively palladium acetate, 4,5-bis(diphenylphosphino)-9,9-dimethylxanthene and cesium carbonate or potassium phosphate, (i) the ruthenium complex prepared from a ruthenium compound and a chiral ligand, (ii) the hydrogen donor and (iii) the base in the step b are respectively (i) a ruthenium-arene complex of the following formula:

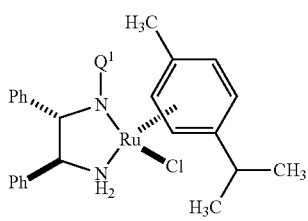

wherein Ph represents a phenyl group, $Q^1$ is a p-toluenesulfonyl group or a benzylsulfonyl group, (ii) formic acid, potassium formate, methanol, or a mixture thereof, and (iii) triethylamine, and the reducing agent in the step c is sodium borohydride or lithium borohydride.

12. The method according to claim 11 in which the reaction in step a is carried out in a mixed solvent of water and an organic solvent.

13. The method according to claim 12 in which the mixed solvent is a mixture of water and toluene.

14. The method according to claim 11 in which the reaction in step a is carried out in the presence of water or a water-donating substance.

15. The method according to claim 14 in which the water-donating substance is sodium sulfate decahydrate or a hydrated zeolite.

16. The method according to claim 1 in which, in the formula [a-1], $X^1$ is a bromine atom and $R^a$ and $R^b$ are each a methyl group.

17. The method according to claim 4 in which the optically active oxazaborolidine compound [R-CBS] is a compound of the following formula [R-CBS1]:

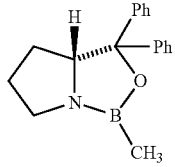

[R-CBS1]

wherein Ph represents a phenyl group,
and the boron hydride compound is a borane complex selected from the group consisting of a borane-tetrahydrofuran complex, a borane-dimethylsulfide complex, a borane-dimethylaniline complex, a borane-diethylaniline complex, a borane-tert-butylamine complex, a borane-triethylamine complex, a borane-pyridine complex and a borane-4-phenylmorpholine complex.

18. The method according to claim 17 in which the boron hydride compound is a borane complex selected from the group consisting of a borane-tetrahydrofuran complex, a borane-dimethylsulfide complex, a borane-diethylaniline complex and a borane-tert-butylamine complex.

19. The method according to claim 16 in which the reaction in the step b is carried out in a solvent selected from the group consisting of dichloromethane and tetrahydrofuran.

20. The method according to claim 1 in which
the reaction of the compound [a-1] with the compound [b-1] is carried out in the presence of a catalyst comprising palladium acetate and 4,5-bis(diphenylphosphino)-9,9-dimethylxanthene, and cesium carbonate or tripotassium phosphate as the base and in the presence of water or sodium sulfate decahydrate as the water-donating substance in a solvent selected from the group consisting of toluene and dimethoxyethane, the asymmetric hydrogenation of the compound [c-1] or a solvate thereof is carried out in the presence of a ruthenium-arene complex of the following formula:

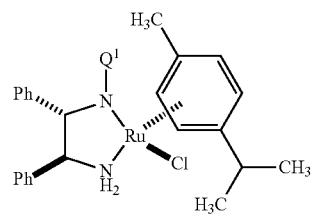

wherein Ph represents a phenyl group and $Q^1$ represents a p-toluenesulfonyl group or a benzylsulfonyl group and one or more compounds as the hydrogen donor selected from the group consisting of formic acid, potassium formate and methanol, and in the presence or absence of triethylamine as the base in a solvent selected from the group consisting of tetrahydrofuran, dimethylacetamide, dimethoxyethane, 2-methyltetrahydrofuran, chlorobenzene, methanol and ethyl acetate, and the reducing reaction of the compound [d-1] or a solvate thereof is carried out in the presence of sodium borohydride as the reducing agent in tetrahydrofuran containing methanol as an additive.

21. The method according to claim 1 in which, in the general formula [a-1], $R^a$ and $R^b$ are each a methyl group and $X^1$ is a bromine atom.

22. The method according to claim 21 in which the solvate of the compound [c-1] is a chlorobenzene monosolvate, a toluene monosolvate or a chloroform monosolvate, and the solvate of the compound [d-1] is an acetonitrile monosolvate.

23. The method according to claim 21 in which a further step of adding water to an ethanol solution of the compound [I] as a reaction product of the step c, followed by collecting the precipitated crystals of compound [I] in a form of 3/2 hydrate is included therein.

24. A method of producing a 3/2 hydrate of a compound of the following formula [I-b]:

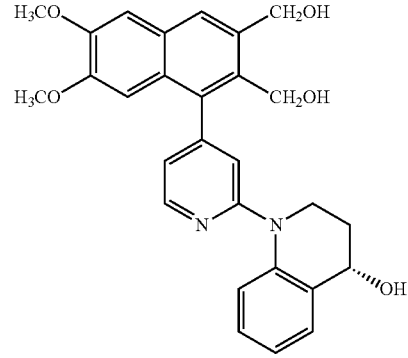

[I-b]

which comprises the following steps of:

(i) reacting a compound of the following formula [a-11]:

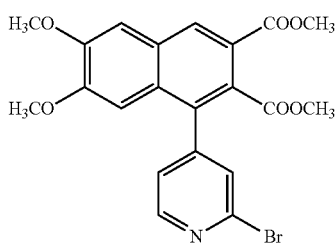
[a-11]

with a compound of the following formula [b-1]:

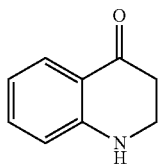
[b-1]

in a solvent in the presence of a catalyst comprising a palladium compound and a tertiary phosphine ligand and a base to produce a compound of the following formula [c-11]:

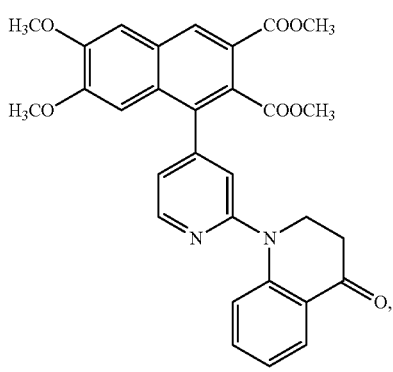
[c-11]

followed by separating and collecting crystals of said compound or a solvate thereof, (ii) subjecting the compound [c-11] or a solvate thereof obtained in the above step (i) to an asymmetric hydrogenation in the presence of a ruthenium complex prepared from a ruthenium compound and a chiral ligand and a hydrogen donor and in the presence or absence of a base to produce a compound of the following formula [d-11]:

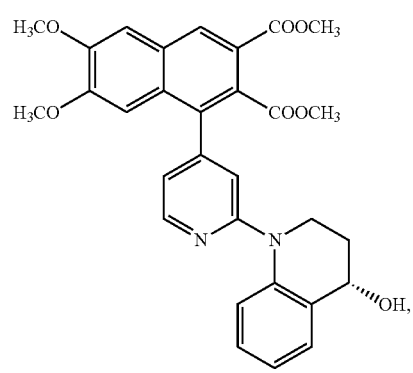
[d-11]

followed by separating and collecting crystals of said compound or a solvate thereof, (iii) treating the compound [d-11] or a solvate thereof obtained in the above step (ii) with a reducing agent in a solvent to produce the compound of the above formula [1-b]; and (iv) crystallizing said reaction product, followed by separating and collecting the obtained crystals.

25. The method according to claim 24 in which the solvate of the compound [c-11] is a chlorobenzene monosolvate, a toluene monosolvate or a chloroform monosolvate, and the solvate of the compound [d-11] is an acetonitrile monosolvate.

26. The method according to claim 24 in which the catalyst comprising a palladium compound and a tertiary phosphine ligand is a catalyst prepared from palladium acetate and a monodentate or bidentate phosphine ligand of the following formula [L-1]:

$$(R^{01})_2P\text{-}Q\text{-}R^{02}$$ [L-1]

wherein $R^{01}$ represents a phenyl group, a tert-butyl group or a cyclohexyl group, Q represents (a) a phenylene group, (b) a biphenylene group optionally substituted by a group selected from the group consisting of a halogen atom and a methoxy group, (c) a ferrocenyl group or (d) a 9,9-dimethylxanthenyl group and $R^{02}$ represents a diphenylphosphino group, a di-tert-butyl-phosphino group or a dimethylamino group, the ruthenium complex prepared from a ruthenium compound and a chiral ligand is a ruthenium-arene complex of the following formula:

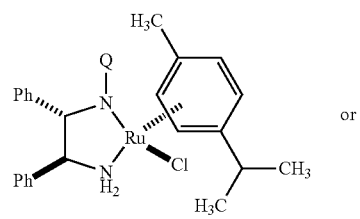
or

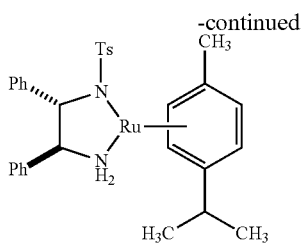

wherein Ph represents a phenyl group, Q represents a methanesulfonyl group, a p-toluenesulfonyl group or a benzylsulfonyl group and Ts represents a p-toluenesulfonyl group, and the reducing agent is sodium borohydride or lithium borohydride.

27. The method according to claim 26 in which the reaction of the compound [a-11] with the compound [b-1] is carried out in a solvent selected from the group consisting of toluene, tetrahydrofuran, dimethylformamide, cyclopentyl methyl ether, chlorobenzene, tert-butanol, N-methylpyrrolidinone, dimethoxyethane and a mixture thereof, the asymmetric hydrogenation of the compound [c-11] or a solvate thereof is carried out in a solvent selected from the group consisting of tetrahydrofuran, 2-methyltetrahydrofuran, 1,2-dimethoxyethane, acetonitrile, chlorobenzene, dimethylformamide, dimethylacetamide, ethyl acetate, isopropyl acetate, methanol and pyridine, and the reducing reaction of the compound [d-11] or a solvate thereof is carried out in a solvent selected from the group consisting of tetrahydrofuran, toluene and a mixture thereof.

28. The method according to claim 24 in which the reaction of the compound [a-11] with the compound [b-1] is carried out in the presence of a catalyst comprising palladium acetate and 4,5-bis(diphenylphosphino)-9,9-dimethylxanthene and cesium carbonate or tripotassium phosphate as the base in a solvent selected from the group consisting of toluene and dimethoxyethane, the asymmetric hydrogenation of the compound [c-11] or a solvate thereof is carried out in the presence of a ruthenium-arene complex of the following formula:

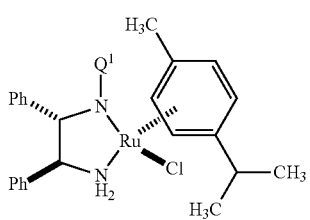

wherein Ph represents a phenyl group, Q¹ is a p-toluenesulfonyl group or a benzylsulfonyl group and one or more compound(s), as the hydrogen donor, selected from the group consisting of formic acid, potassium formate and methanol and in the presence or absence of triethylamine as the base in a solvent selected from the group consisting of tetrahydrofuran, dimethylacetamide, dimethoxyethane, 2-methyltetrahydrofuran, chlorobenzene, methanol and ethyl acetate, and the reducing reaction of the compound [d-11] or a solvate thereof is carried out in the presence of sodium borohydride as the reducing agent in tetrahydrofuran containing methanol as an additive.

29. The method according to claim 24 in which the asymmetric hydrogenation of the compound [c-11] or a solvate thereof is carried out in methanol, N-methylpyrrolidone; water or a mixture thereof as the solvent.

30. The method according to claim 24 in which the asymmetric hydrogenation of the compound [c-11] or a solvate thereof is carried out in the presence of methanol as the hydrogen donor in dichloromethane, N-methylpyrrolidone or 1,3-dimethylimidazolidinone as the solvent.

31. The method according to claim 28 in which the asymmetric hydrogenation of the compound [c-11] or a solvate thereof is carried out in the presence of potassium formate and methanol as the hydrogen donor and in chlorobenzene as the solvent.

32. The method according to claim 28 in which the asymmetric hydrogenation of the compound [c-11] or a solvate thereof is carried out in the presence of formic acid as the hydrogen donor and in tetrahydrofuran as the solvent.

33. A compound of the following formula [c-11]:

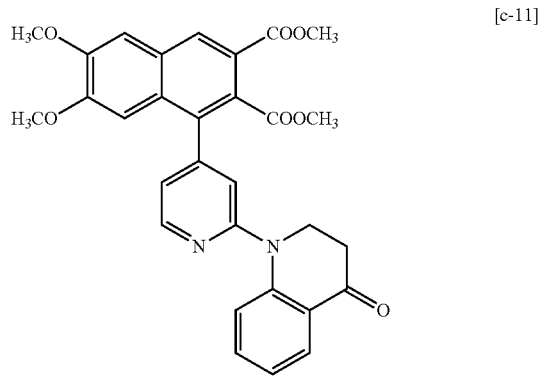 [SMILES: COC(=O)c1cc2cc(OC)c(OC)cc2c(-c2ccnc(N3CCC(=O)c4ccccc43)c2)c1C(=O)OC]

or a solvate thereof.

34. A chlorobenzene monosolvate, a toluene monosolvate or a chloroform monosolvate of the compound [c-11] according to claim 33.

35. A compound of the following formula [d-11]:

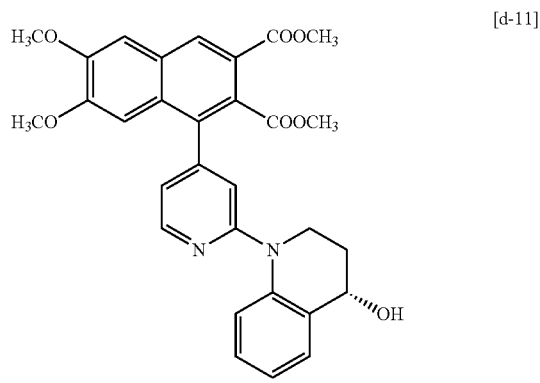 [SMILES: COC(=O)c1cc2cc(OC)c(OC)cc2c(-c2ccnc(N3CC[C@H](O)c4ccccc43)c2)c1C(=O)OC]

or a solvate thereof.

36. An acetonitrile monosolvate of the compound [d-11] according to claim 35.

* * * * *